(12) United States Patent
Ishikawa et al.

(10) Patent No.: US 10,379,070 B2
(45) Date of Patent: Aug. 13, 2019

(54) POWER MODULE

(71) Applicant: Mitsubishi Electric Corporation, Chiyoda-ku (JP)

(72) Inventors: Shuta Ishikawa, Chiyoda-ku (JP); Teruaki Tanaka, Chiyoda-ku (JP)

(73) Assignee: Mitsubishi Electric Corporation, Chiyoda-ku (JP)

( * ) Notice: Subject to any disclaimer, the term of this patent is extended or adjusted under 35 U.S.C. 154(b) by 874 days.

(21) Appl. No.: 14/771,091

(22) PCT Filed: Feb. 19, 2014

(86) PCT No.: PCT/JP2014/053872
§ 371 (c)(1),
(2) Date: Aug. 27, 2015

(87) PCT Pub. No.: WO2014/141835
PCT Pub. Date: Sep. 18, 2014

(65) Prior Publication Data
US 2016/0003754 A1    Jan. 7, 2016

(30) Foreign Application Priority Data

Mar. 15, 2013  (JP) ................... 2013-053529

(51) Int. Cl.
*G01N 25/72*    (2006.01)
*H02M 7/5387*   (2007.01)
(Continued)

(52) U.S. Cl.
CPC ........ *G01N 25/72* (2013.01); *H02M 7/53871* (2013.01); *H01L 2224/32225* (2013.01);
(Continued)

(58) Field of Classification Search
CPC .............. G01N 25/72; H02M 7/53871; H02M 2001/0003; H02M 2001/327; H01L 2224/32225

See application file for complete search history.

(56) References Cited

U.S. PATENT DOCUMENTS

2003/0076232 A1    4/2003  Sato et al.
2005/0071090 A1    3/2005  Katou
(Continued)

FOREIGN PATENT DOCUMENTS

CN    101087125 A    12/2007
CN    101299577 A    11/2008
(Continued)

OTHER PUBLICATIONS

International Search Report dated Jun. 3, 2014 in PCT/JP14/053872 Filed Feb. 19, 2014.
(Continued)

*Primary Examiner* — Regis J Betsch
*Assistant Examiner* — Jeremy A Delozier
(74) *Attorney, Agent, or Firm* — Oblon, McClelland, Maier & Neustadt, L.L.P.

(57) ABSTRACT

An A/D converter converts an output from a temperature sensor into a digital signal. A service life diagnostic unit diagnoses a service life of a power module based on a signal indicating a temperature outputted from the A/D converter. An output unit generates a signal representing a diagnostic result and outputs the generated signal from an output terminal to outside.

19 Claims, 31 Drawing Sheets

(51) Int. Cl.
*H02M 1/00* (2006.01)
*H02M 1/32* (2007.01)

(52) U.S. Cl.
CPC ............... *H02M 2001/0003* (2013.01); *H02M 2001/327* (2013.01)

(56) References Cited

U.S. PATENT DOCUMENTS

2008/0262750 A1* 10/2008 Ibori .................... H02M 5/451
702/34
2015/0204730 A1* 7/2015 Daitoku ................... G01K 7/01
374/178

FOREIGN PATENT DOCUMENTS

| CN | 100477467 C | 4/2009 |
|---|---|---|
| CN | 101533064 A | 9/2009 |
| JP | 10 38960 | 2/1998 |
| JP | 10 197588 | 7/1998 |
| JP | 11 285155 | 10/1999 |
| JP | 11 344466 | 12/1999 |
| JP | 2002 101668 | 4/2002 |
| JP | 2003 134795 | 5/2003 |
| JP | 2005 354812 | 12/2005 |
| JP | 2007 240805 | 9/2007 |
| JP | 2009 17707 | 1/2009 |
| JP | 2011 196703 | 10/2011 |
| JP | 2012 10457 | 1/2012 |

OTHER PUBLICATIONS

Combined Chinese Office Action and Search Report dated Dec. 28, 2016 in Patent Application No. 201480015591.8 (with English Translation and English Translation of Category of Cited Documents).

* cited by examiner

FIG.12

| SL | OUTPUT |
|----|--------|
| 00 | MAXIMUM VALUE OF Suns, Svns, Swns |
| 01 | Suns |
| 10 | Svns |
| 11 | Swns |

FIG.22

| SL | OUTPUT |
|---|---|
| 000 | MAXIMUM VALUE OF Sups, Svps, Swps, Suns, Svns, Swns |
| 001 | Sups |
| 010 | Svps |
| 011 | Swps |
| 100 | Suns |
| 101 | Svns |
| 110 | Swns |
| 111 | MINIMUM VALUE OF Sups, Svps, Swps, Suns, Svns, Swns |

POWER MODULE

TECHNICAL FIELD

The present invention relates to a power module, and more particularly to a power module which performs a power conversion operation with integrated power semiconductor elements.

BACKGROUND ART

Various power modules such as an inverter for driving an alternating-current motor, a power conditioner for solar power generation, and the like are electric components configured to perform a power conversion operation with integrated semiconductor elements.

Such a power module is provided by integrating not only semiconductor elements but also a case, a sealing gel, an electric interconnection, an insulating substrate, and a base plate. Further, a gate driver circuit and a protection circuit for preventing overheat and overcurrent are also integrated, depending on a kind of a power module. Therefore, convenience for a user who designs and manufactures a product using a power module is provided.

Since a sudden failure of a power module leads to stop equipment and a device to which the power module is applied, it causes economical loss and the like. Therefore, there has been a known attempt to diagnose a service life of a power module.

For example, according to the method disclosed in Japanese Patent Laying-Open No. 2011-196703 (PTD 1), an entire operational temperature range of a semiconductor device constituted of power semiconductor elements is divided into a plurality of temperature regions, and the number of cycles is calculated with use of values weighted to the number of power cycles in respectively set reference temperature differences within the temperature region. Further, according to this method, the service life is estimated by calculating an accumulated damage with use of the Miner's law based on each of the calculated number of cycles between the divided temperature regions.

CITATION LIST

Patent Document

PTD 1: Japanese Patent Laying-Open No. 2011-196703

SUMMARY OF INVENTION

Technical Problem

According to the method for estimating a service life of a power module disclosed in Japanese Patent Laying-Open No. 2011-196703 (PTD 1), one temperature sensor is provided since a service life of a single semiconductor chip is diagnosed.

However, since a power module such as a three-phase two-level inverter has different reference potentials for respective three upper arms and a lower arm, there exists four reference potentials in total. Therefore, it would be necessary to provide at least four A/D converters and insulating elements, so that the size of the power module becomes greater.

Further, according to the power module disclosed in Japanese Patent Laying-Open No. 2011-196703 (PTD 1), a configuration of outputting a diagnostic result of a service life to outside is not disclosed.

Therefore, an object of the present invention is to provide a power module for which a small-scale service life diagnostic can be performed and from which a diagnostic result of a service life can be outputted to outside.

Solution to Problem

To solve the problem described above, a power module of the present invention comprises a plurality of semiconductor chips, one or more temperature sensor provided in a periphery of at least one semiconductor chip of the plurality of semiconductor chips, one A/D converter which converts an output from the temperature sensor into a digital signal, and a diagnostic unit which diagnoses a service life of the power module based on a signal indicating a temperature outputted from the A/D converter. The power module of the present invention further comprises an output unit which generates a signal representing a diagnostic result and an output terminal which outputs a signal representing the diagnostic result to outside.

Advantageous Effects of Invention

According to the present invention, a service life diagnosis can be performed on a small scale. Moreover, a service life diagnostic result can be outputted to outside.

BRIEF DESCRIPTION OF DRAWINGS

FIG. 12 represents a relationship between a select signal SL and an outputted deterioration ratio in the second embodiment.

FIG. 22 represents a relationship between a select signal SL and an outputted deterioration ratio in the third embodiment.

DESCRIPTION OF EMBODIMENTS

Hereinafter, embodiments of the present invention will be described with reference to the drawings.

First Embodiment

Figure 1:
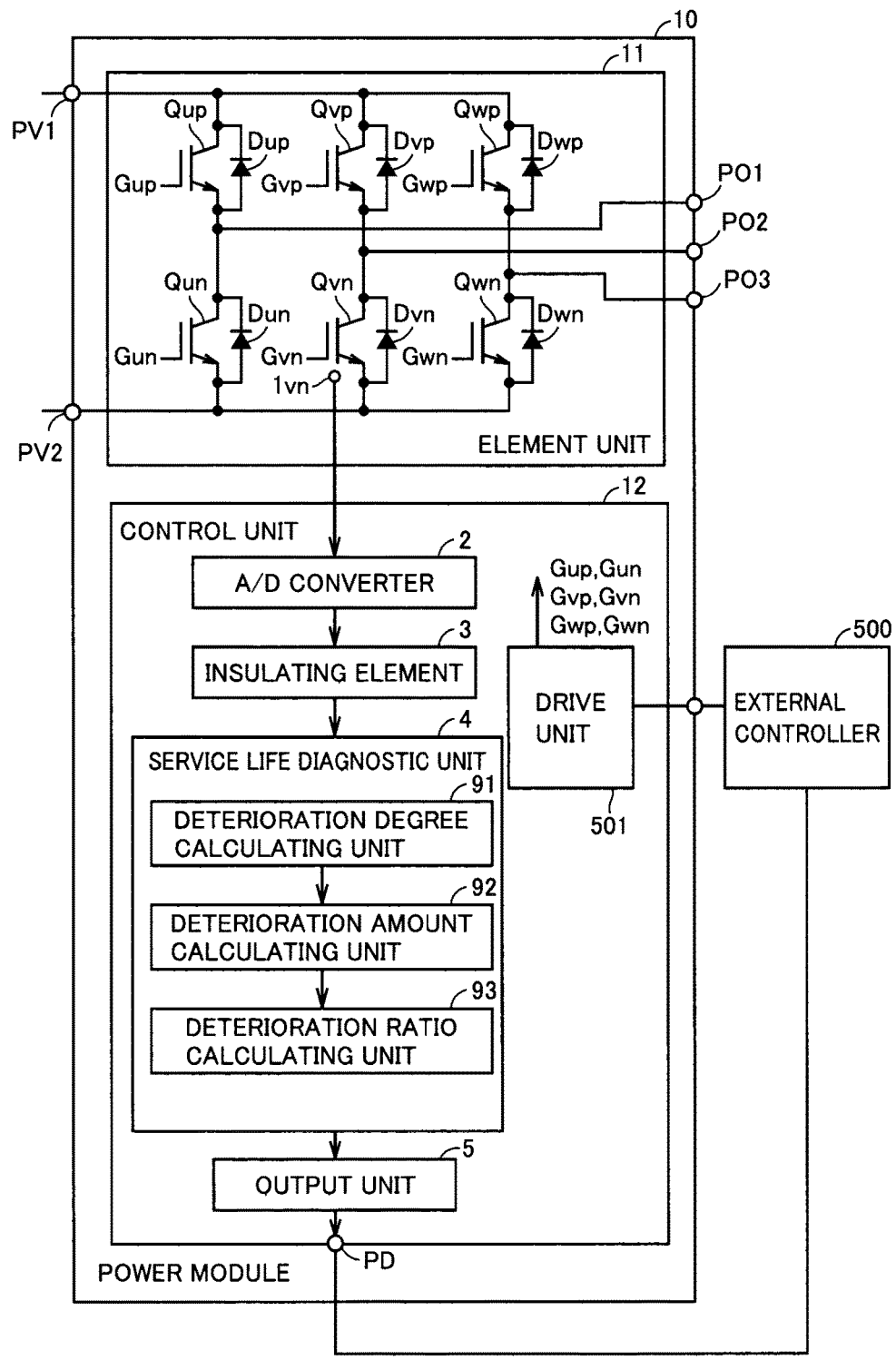
FIG. 1 represents a configuration of a power module in accordance with a first embodiment.

FIG. 1 represents a configuration of a power module in accordance with a first embodiment.

Figure 2:
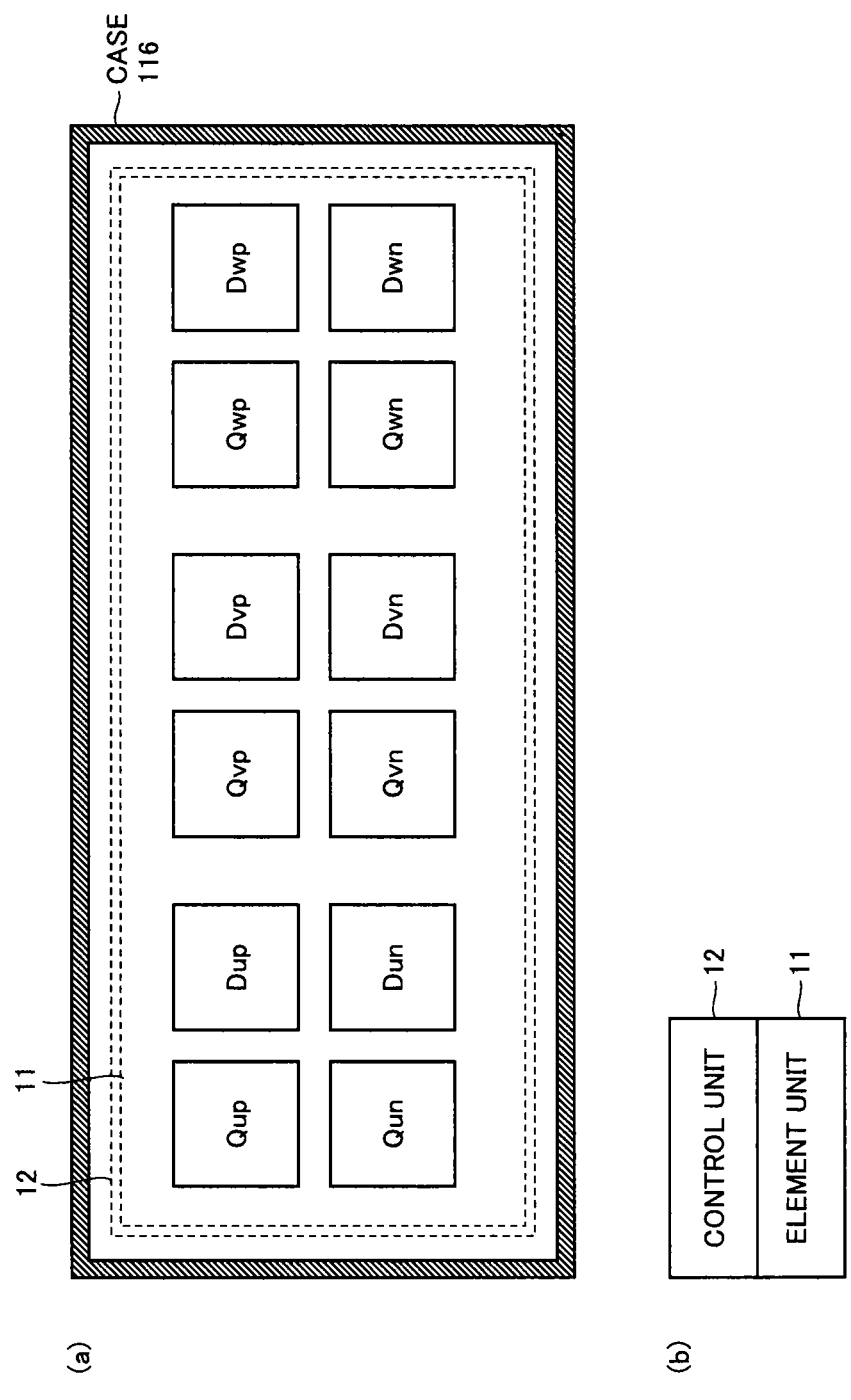
FIG. 2 is a diagram for illustrating a layout of a power module.
Figure 3:
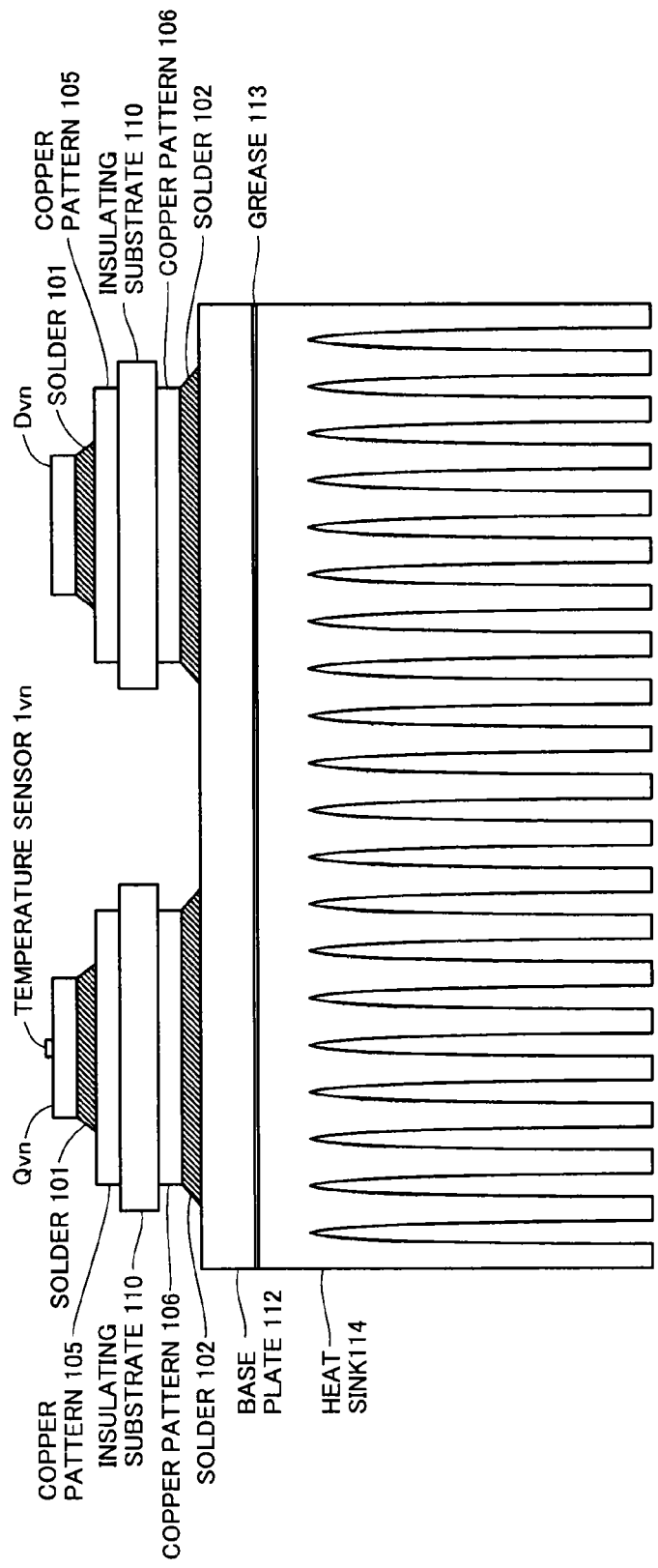
FIG. 3 is a diagram for illustrating a layout of a power module.

FIGS. 2 and 3 are diagrams for illustrating layouts of the power module.

As shown in FIG. 1, this power module includes an element unit 11, a temperature sensor 1vn, and a control unit 12.

Element unit 11 is a portion constituted of twelve elements in total including IGBT chips and diode chips used for converting inputted direct-current electric power into three-phase alternating-current electric power.

Element unit 11 includes switching elements Qup, Qvp, Qwp, Qun, Qvn, Qwn and diode elements Dup, Dvp, Dwp, Dun, Dvn, Dwn for a current reflux. Switching elements Qup, Qvp, Qwp, Qun, Qvn, Qwn and diode elements Dup, Dvp, Dwp, Dun, Dvn, Dwn for a current flux are respectively constituted of independent semiconductor chips. Switching elements Qup, Qvp, Qwp, Qun, Qvn, Qwn are IGBTs (Insulated-Gate Bipolar Transistors).

A positive electrode-side node of element unit 11 is connected to a voltage terminal PV1, and a negative electrode-side node is connected to a voltage terminal PV2. A U-phase output of element unit 11 is connected to an output terminal PO1. A V-phase output is connected to an output terminal PO2. A W-phase output is connected to an output terminal PO3.

Switching elements Qup, Qun (U-phase arms) are connected in this order in series between the positive electrode-side node and the negative electrode-side node. Switching elements Qvp, Qvn (V-phase arms) are connected in this order in series between the positive electrode-side node and the negative electrode-side node, and in parallel with the U-phase arms. Switching elements Qwp, Qwn (W-phase arms) are connected in this order in series between the positive electrode-side node and the negative electrode-side node, and in parallel with the U-phase and V-phase arms. Diode elements Dup, Dun, Dvp, Dvn, Dwp, Dwn are connected respectively to switching elements Qup, Qun, Qvp, Qvn, Qwp, Qwn in parallel and in the reverse bias direction.

Switching elements Qup, Qvp, Qwp and diode elements Dup, Dvp, Dwp constitute upper arms. Switching elements Qun, Qvn, Qwn and diode elements Dun, Dvn, Dwn constitute lower arms.

As shown in FIG. 3, in a periphery of switching element Qvn and diode element Dvn, layers of solder 101, 102 connecting members, copper patterns 105, 106 allowing a current to flow, insulating substrates 110 providing electric insulation, a base plate 112 for radiating heat and holding members, and the like are provided respectively. It should be noted that FIG. 3 also shows a heat sink 114 connected to the power module and grease 113 for reducing a contact thermal resistance. Moreover, an electric interconnection such as wire bonding, case gel, and the like are omitted from the drawing. A layout of switching element Qup and diode element Dup, a layout of switching element Qvp and diode element Dvp, a layout of switching element Qwp and diode element Dwp, a layout of switching element Qun and diode element Dun, and a layout of switching element Qwn and diode element Dwn are also similar to the layout of FIG. 3 except that a temperature sensor is not provided.

Since the power module handles a relatively great electric power, there is a remarkable temperature change inside the power module due to a power loss. Therefore, although each member expands and contracts in accordance with this temperature change, the degree of expansion and contraction is different in accordance with a material of each member. Therefore, a great stress is generated between members to cause thermal fatigue in the members. Particularly, a breakage by development of a crack (split) due to the thermal fatigue is likely to occur in solder 101 provided directly under switching element Qup as a semiconductor chip and diode element Dup. Moreover, the thermal fatigue is likely to occur at a joining portion between switching element Qup as a semiconductor chip and a bonding wire (not shown).

A service life of the power module determined based on a failure due to the crack in solder 101 and a failure of the joining portion between the switching element and the bonding wire is referred to as a so-called power cycle service life, and it is one of the main failure modes of the power module. It should be noted that, in the following paragraphs, the development of the crack in solder 101 and peeling at the joining portion between the switching element and the bonding wire are referred to as "deterioration."

A temperature sensor 1vn is provided in a periphery of switching element Qvn, in other words, in a periphery where a temperature of solder 101 and the joining portion between switching element Qvn and the bonding wire can be detected, and detects a temperature in the periphery.

As shown in FIG. 2(a), six switching elements Qup, Qvp, Qwp, Qun, Qvn, Qwn and six diode elements Dup, Dvp, Dwp, Dun, Dvn, Dwn are arranged intensively in a case 116.

As shown in FIG. 2(b), control unit 12 is arranged on an upper layer of element unit 11.

As shown in FIG. 1, control unit 12 includes a drive unit 501, an A/D converter 2, an insulating element 3, a service life diagnostic unit 4, an output unit 5, and an output terminal PD. Service life diagnostic unit 4 includes deterioration a degree calculating unit 91, a deterioration amount calculating unit 92, and a deterioration ratio calculating unit 93.

Drive unit 501 outputs control signals Gup, Gun, Gyp, Gvn, Gwp, Gwn to switching elements Qup, Qun, Qvp, Qvn, Qwp, Qwn.

A/D converter 2 converts an analog signal representing a temperature transmitted from temperature sensor 1vn into a digital signal.

A digital signal Tvn(t) representing a temperature at a time t outputted from A/D converter 2 is transmitted to service life diagnostic unit 4 through insulating element 3. Insulating element 3 is provided to prevent malfunction and failure in service life diagnostic unit 4.

Service life diagnostic unit 4 is constituted of an FPGA (Field Programmable Gate Array), an ASIC (Application Specific Integrated Circuit), a microprocessor, or a combination of those.

Figure 4:
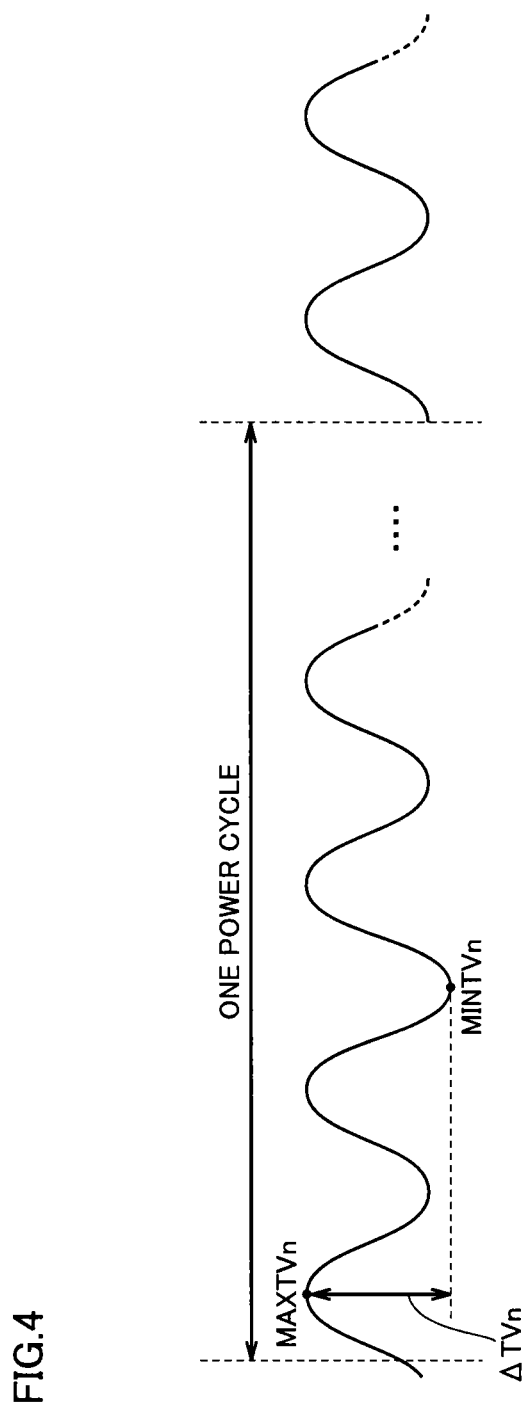
FIG. 4 represents a change in a temperature detected by a temperature sensor within one power cycle.

As shown in FIG. 4, deterioration degree calculating unit 91 derives a maximum temperature MAXTvn and a minimum temperature MINTvn in one power cycle from temperature Tvn(t) at each time t within one power cycle. Further, deterioration degree calculating unit 91 calculates a difference between maximum temperature MAXTvn and minimum temperature MINTvn to derive a pulsation temperature $\Delta$Tvn in one power cycle. Herein, the one power cycle corresponds to one cycle of a temperature change in the semiconductor chip.

$$\Delta Tvn = MAX\ Tvn - MIN\ Tvn \quad (A1)$$

Deterioration degree calculating unit 91 calculates a power cycle number Nvnf of an expected service life of switching element Qvn in accordance with the following Arrhenius form expression (A2) from maximum temperature MAXTvn, minimum temperature MINTvn, and pulsation temperature $\Delta$Tvn in one power cycle. The Arrhenius form expression (A2) represents a service life characteristic in a power cycle of switching element Qvn (semiconductor chip).

[Expression 1]

$$Nvnf = A \cdot \Delta Tvn^{\alpha} \cdot \exp\left[\frac{B}{MAXTvn + MINTvn}\right] \quad (A2)$$

Herein, A, B, and a are coefficients and determined from an expected service life of a power cycle of switching element Qvn.

Deterioration degree calculating unit 91 calculates a deterioration degree Rvn of switching element Qvn in one power cycle in accordance with the following expression (A3).

$$Rvn = 1/Nvnf \quad (A3)$$

Deterioration amount calculating unit 92 calculates a deterioration amount Svn, which is a deterioration amount of switching element Qvn, in accordance with the following expression (A4).

$$Svn = Svn + Rvn \quad (A4)$$

Deterioration ratio calculating unit 93 calculates a deterioration ratio Svns of switching element Qvn by dividing deterioration amount Svn of switching element Qvn by a deterioration amount SMAX provided after having reached an expected service life in accordance with the expression (A5). Deterioration ratio Svns represents a ratio of a consumed service life with respect to an expected service life of switching element Qvn.

$$Svns = Svn/S\ MAX \quad (A5)$$

In the present embodiment, a service life (deterioration ratio) of one switching element Qvn is regarded as a service life (deterioration) of an entire power module. This utilizes the feature that a current flows to all elements with good balance and temperatures of all elements change similarly in a general power module.

(Operation of Service Life Diagnosis)

Figure 5:
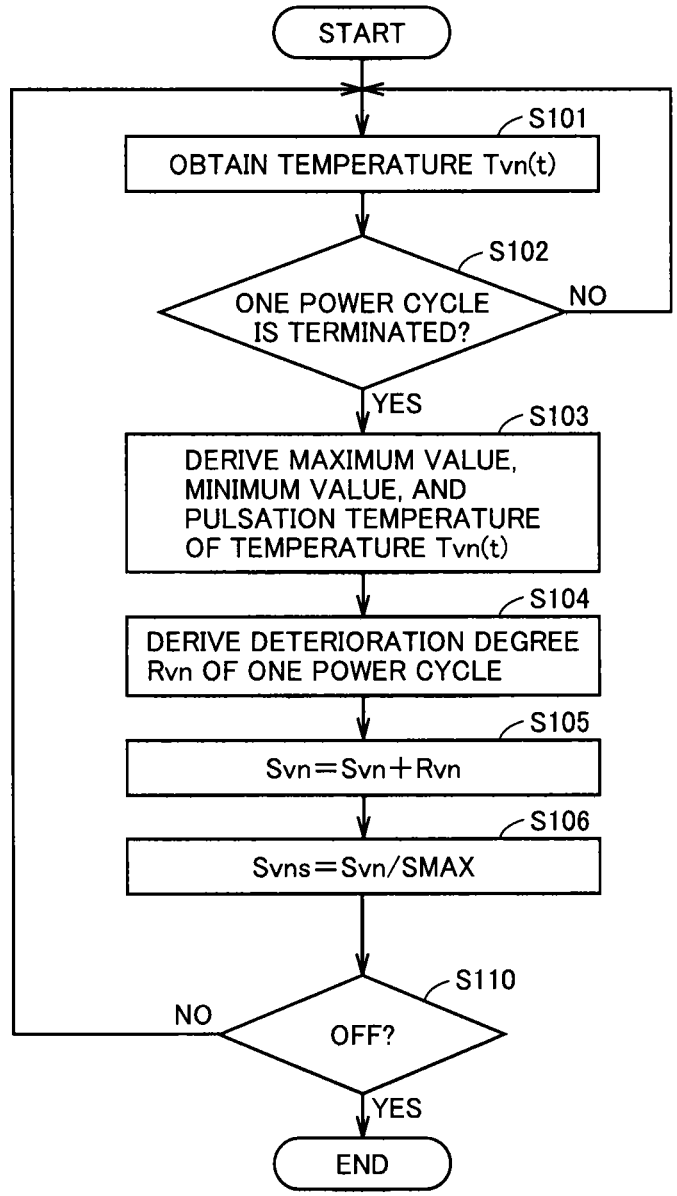
FIG. 5 is a flowchart representing operation procedures for a service life diagnosis of the first embodiment.

FIG. 5 is a flowchart representing operation procedures for the service life diagnosis of the first embodiment.

Referring to FIG. 5, firstly, deterioration degree calculating unit 91 obtains temperature Tvn(t) from A/D converter 2 (Step S101).

Next, when one power cycle is terminated (YES in Step S102), deterioration degree calculating unit 91 derives maximum temperature MAXTvn, minimum temperature MINTvn, and pulsation temperature $\Delta$Tvn of temperature Tvn(t) within one power cycle (Step S103).

Next, deterioration degree calculating unit 91 calculates deterioration degree Rvn of switching element Qvn in one power cycle in accordance with expressions (A2) and (A3) (Step S104).

Next, deterioration amount calculating unit 92 calculates a sum total of deterioration degree Rvn per power cycle as deterioration amount Svn of switching element Qvn in accordance with expression (A4) (Step S105).

Next, deterioration ratio calculating unit 93 calculates deterioration ratio Svns of switching element Qvn by dividing deterioration amount Svn of switching element Qvn by deterioration amount SMAX provided after having reached an expected service life in accordance with expression (A5) (Step S106).

When a power supply is in an on-state (NO in Step S110), the processing from Step S101 is repeated. Moreover, when the power supply is turned off (YES in Step S110), the processing is terminated.

Figure 6:
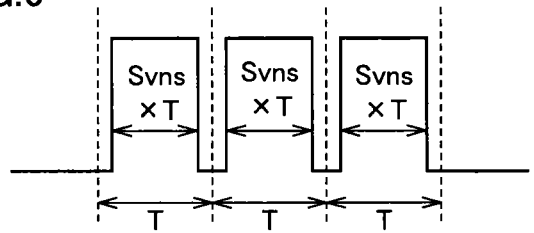
FIG. 6 represents an example of a signal outputted from an output terminal PD in the first embodiment.

As shown in FIG. 6, output unit 5 generates a signal setting deterioration ratio Svns of switching element Qvn to be an on-pulse duty ratio per power cycle, and outputs the same from output terminal PD. Instead of expressing deterioration ratio Svns with an on-pulse duty ratio, it may be expressed with an off-pulse duty ratio.

As described above, according to the present embodiment, the number of A/D converters or insulating elements can be reduced, so that the service life diagnosis can be performed with a small circuit configuration. Consequently, increase in size of the power module can be prevented.

Modified Example 1 of First Embodiment

Figure 7:
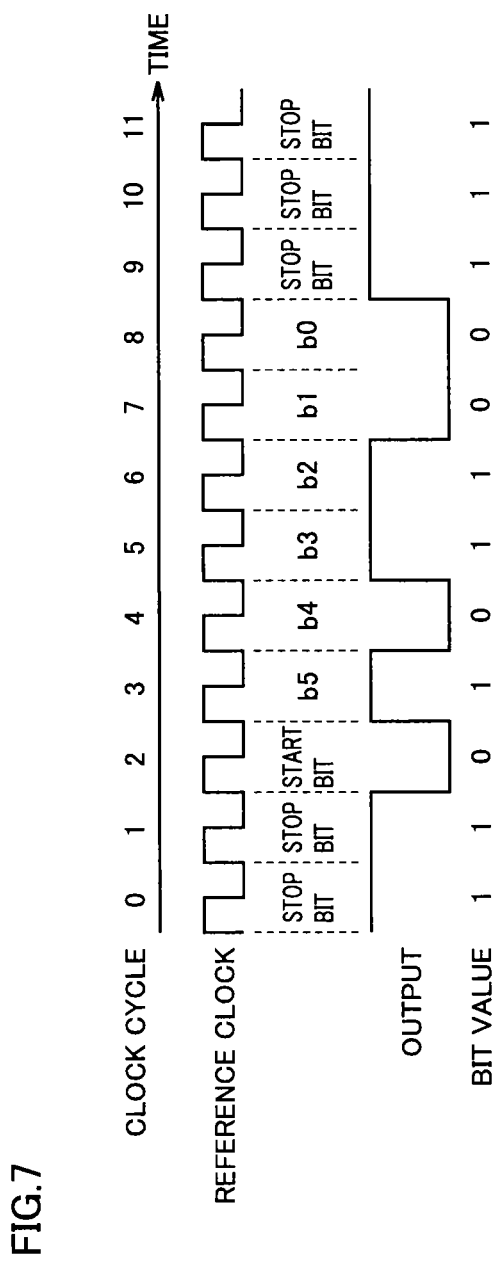
FIG. 7 represents an example of a signal outputted from an output terminal PD in a modified example 1 of the first embodiment.

FIG. 7 represents an example of a signal outputted from output terminal PD in a modified example 1 of the first embodiment.

Output unit 5 converts deterioration ratio Svns of switching element Qvn into G-bit digital values b0 to b5.

As shown in FIG. 7, output unit 5 generates a serial signal including a start bit, deterioration ratio Svns (b0 to b5), and stop bits per power cycle, and outputs the same from output terminal PD.

It should be noted that, although the deterioration ratio is expressed by 6-bits in the modified example described above, this is one example, and the deterioration ratio may be expressed by n-bits (n is a natural number greater than or equal to 1).

Modified Example 2 of First Embodiment

Figure 8:
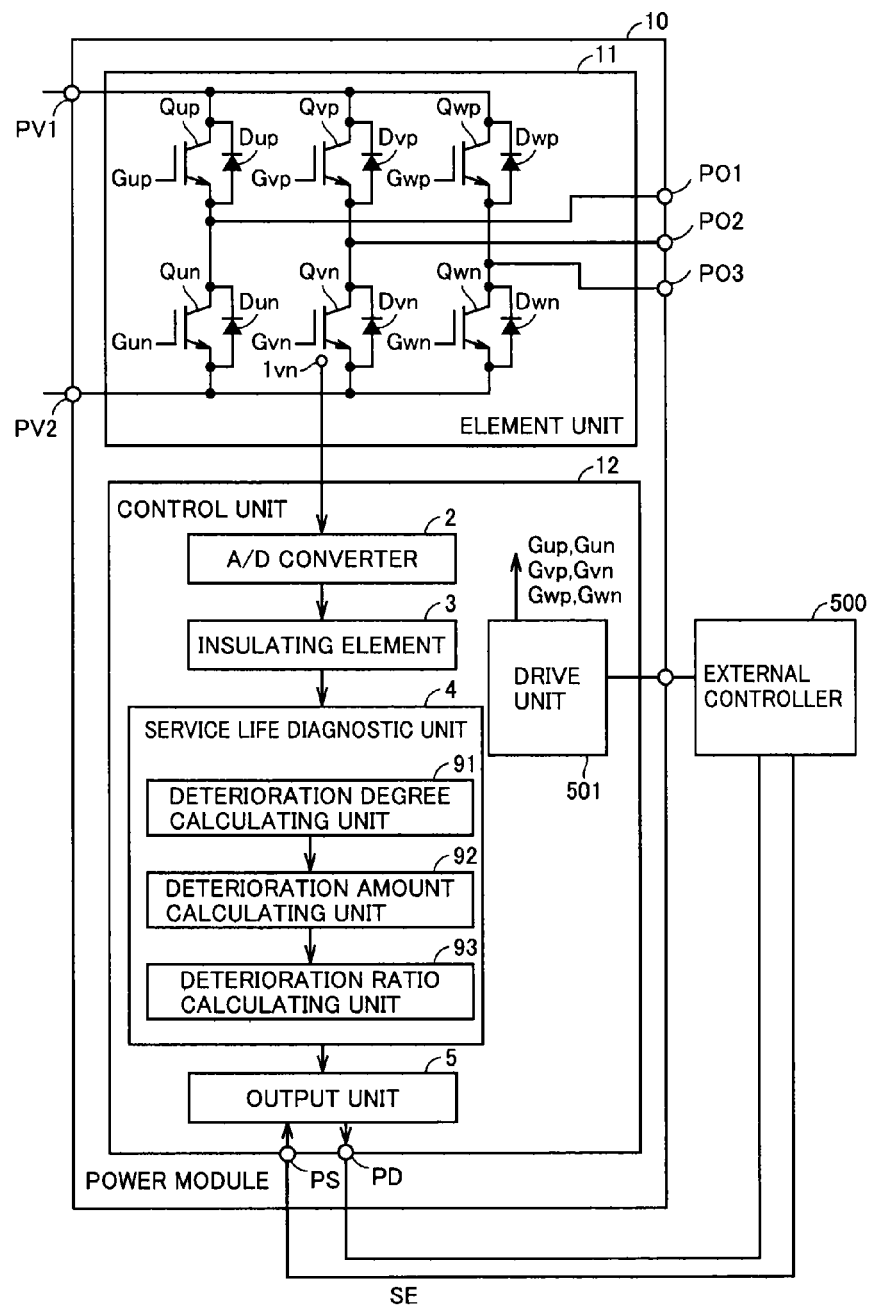
FIG. 8 represents a configuration of a power module of a modified example 2 of the first embodiment.

FIG. 8 represents a configuration of a power module of a modified example 2 of the first embodiment.

This power module 10 includes a select terminal PS.

An external control unit 500 transmits a 1-bit select signal SE through select terminal PS. When select signal SE is "1," output unit 5, similarly to the first embodiment, generates a signal setting deterioration ratio Svns of switching element Qvn to be an on-pulse duty ratio per power cycle as shown in FIG. 6, and outputs the same from output terminal PD. Instead of expressing deterioration ratio Svns with an on-pulse duty ratio, it may be expressed by an off-pulse duty ratio. When select signal SE is "0," output unit 5, similarly to modified example 1 of the first embodiment, generates a serial signal including a start bit, deterioration ratio Svns (b0 to b5), and stop bits per power cycle as shown in FIG. 7, and outputs the same from output terminal PD.

Modified Example 3 of First Embodiment

Figure 9:
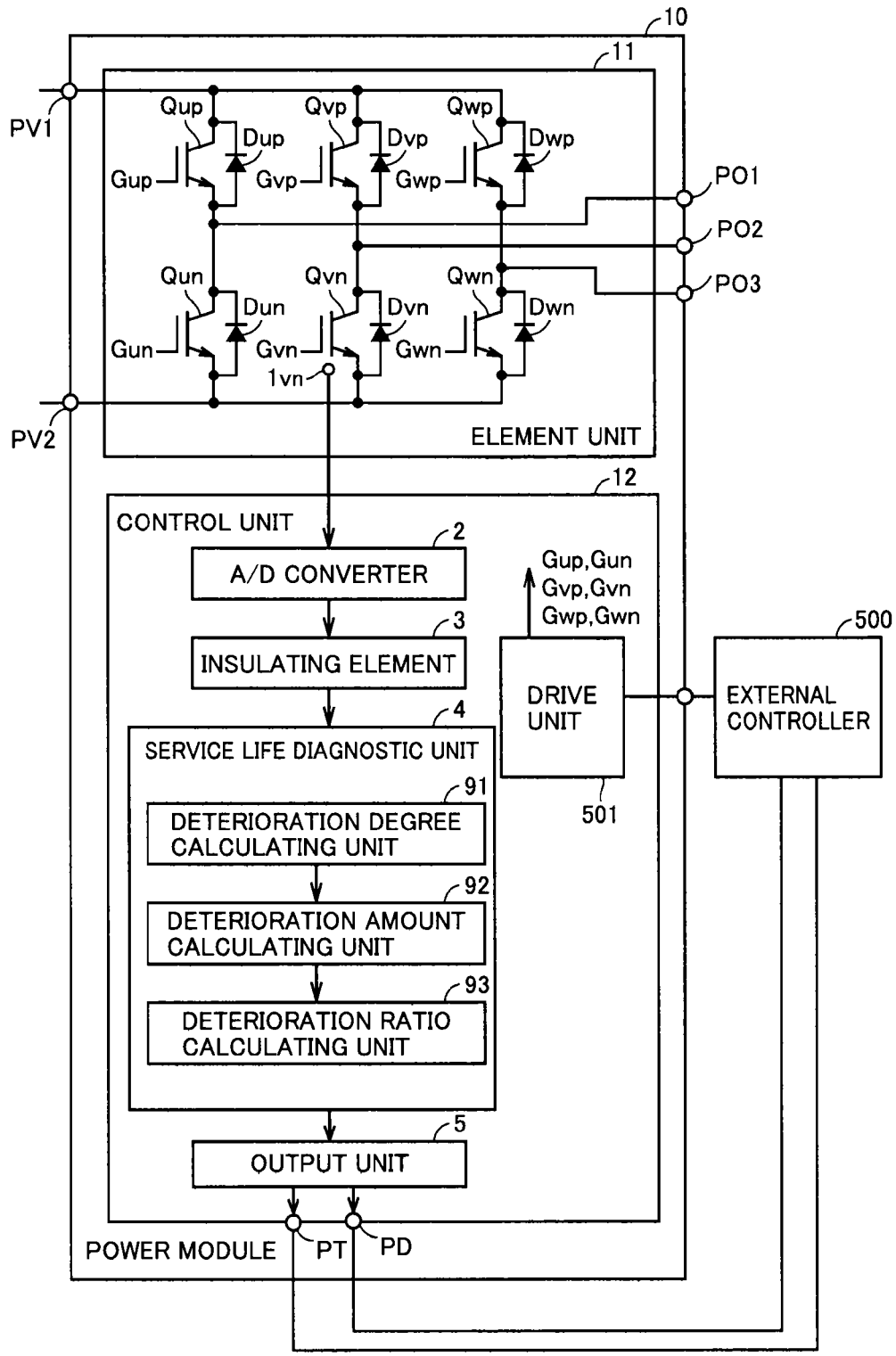
FIG. 9 represents a configuration of a power module of a modified example 3 of the first embodiment.

FIG. 9 represents a configuration of a power module of a modified example 3 of the first embodiment.

This power module 10 includes an output terminal PT.

Output unit 5 generates a serial signal including a start bit, 6-bit maximum temperature MAXTvn, 6-bit minimum temperature MINTvn, 6-bit pulsation temperature ΔTvn, and stop bits per power cycle, and outputs the same from output terminal PT.

It should be noted that output unit 5 may output only one of maximum temperature MAXTvn, minimum temperature MINTvn, and pulsation temperature ΔTvn from output terminal PT. Moreover, output unit 5 may output an average temperature per power cycle.

It should be noted that, although the temperature is expressed by 6-bits in the modified example described above, this is one example, and the temperature may be expressed by n-bits (n is a natural number greater than or equal to 1).

Second Embodiment

Figure 10:
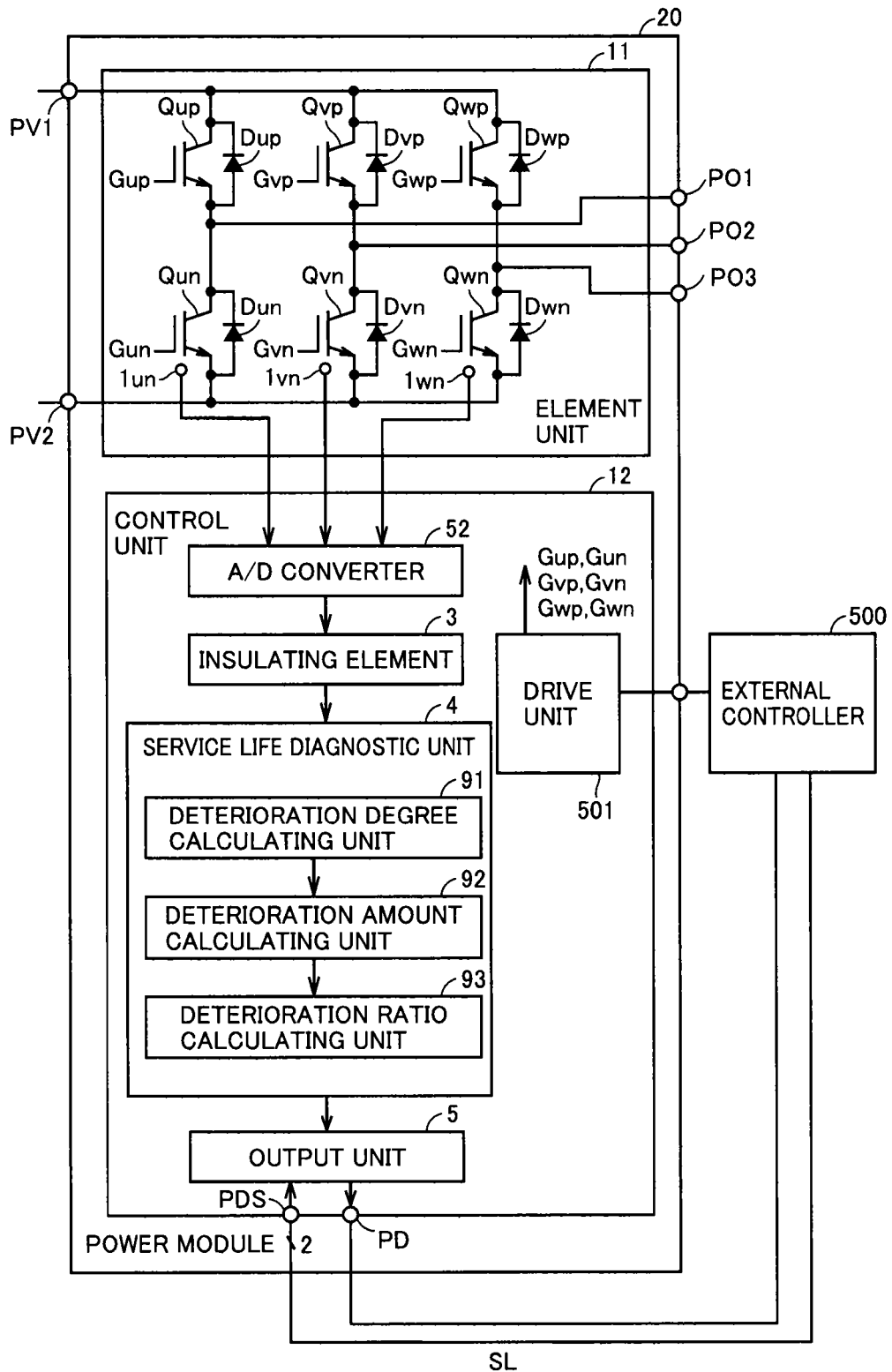
FIG. 10 represents a configuration of a power module of a second embodiment.

FIG. 10 represents a configuration of a power module of a second embodiment.

A power module 20 of FIG. 10 is different from power module 10 of FIG. 1 on the following points.

Power module 20 includes temperature sensors 1un, 1vn, 1wn.

Temperature sensor 1un is arranged in a periphery of switching element Qun, in other words, in a periphery where the temperature of solder 101 and a joining portion between switching element Qun and a bonding wire can be detected, and detects the temperature in that periphery.

Temperature sensor 1vn is arranged in a periphery of switching element Qvn, in other words, in a periphery where the temperature of solder 101 and a joining portion between switching element Qvn and a bonding wire can be detected, and detects the temperature in that periphery.

Temperature sensor 1wn is arranged in a periphery of switching element Qwn, in other words, in a periphery where the temperature of solder 101 and a joining portion between switching element Qwn and a bonding wire can be detected, and detects the temperature in that periphery.

A/D converter 52 converts analog signals representing temperatures transmitted from temperature sensors 1un, 1vn, 1wn into digital signals. A/D converter 52 has three input channels and one output channel. By sequentially designating input channels for the A/D conversion, signals from temperature sensors 1un, 1vn, 1wn are converted into digital signals.

Digital signals Tun(t), Tvn(t), Twn(t) representing temperatures outputted from A/D converter 52 are transmitted to service life diagnostic unit 4 through insulating element 3.

Insulating element 3 is provided to prevent malfunction and failure of service life diagnostic unit 26.

Deterioration degree calculating unit 91 derives maximum temperature MAXTun and minimum temperature MINTun in one power cycle from temperature Tun(t) at each time t within one power cycle. Further, deterioration degree calculating unit 91 calculates a difference between maximum temperature MAXTun and minimum temperature MINTun to derive pulsation temperature ΔTun in one cycle.

$$\Delta Tun = \text{MAX } Tun - \text{MIN } Tun \tag{B1}$$

Deterioration degree calculating unit 91 derives maximum temperature MAXTvn and minimum temperature MINTvn in one power cycle from temperature Tvn(t) of each time t within one power cycle. Further, deterioration degree calculating unit 91 calculates a difference between maximum temperature MAXTvn and minimum temperature MINTvn to derive pulsation temperature ΔTvn in one power cycle.

$$\Delta Tvn = \text{MAX } Tvn - \text{MIN } Tvn \tag{B2}$$

Deterioration degree calculating unit 91 derives maximum temperature MAXTwn and minimum temperature MINTwn in one power cycle from temperature Twn(t) at each time t within one power cycle. Further, deterioration degree calculating unit 91 calculates a difference between maximum temperature MAXTwn and minimum temperature MINTwn to derive pulsation temperature ΔTwn in one power cycle.

$$\Delta Twn = \text{MAX } Twn - \text{MIN } Twn \tag{B3}$$

Deterioration degree calculating unit 91 calculates a power cycle number Nunf of an expected service life of switching element Qun from maximum temperature MAXTun, minimum temperature MINTun, and pulsation temperature ΔTun in one power cycle in accordance with the following Arrhenius form expression (B4). The Arrhenius form expression (B4) represents a service life characteristic in a power cycle of switching element Qun (semiconductor chip).

[Expression 2]

$$Nunf = A \cdot \Delta Tun^{\alpha} \cdot \exp\left[\frac{B}{\text{MAX}Tun + \text{MIN}Tun}\right] \tag{B4}$$

Deterioration degree calculating unit 91 calculates power cycle number Nvnf of an expected service life of switching element Qvn from maximum temperature MAXTvn, minimum temperature MINTvn, and pulsation temperature ΔTvn in one power cycle in accordance with the following Arrhenius form expression (B5). The Arrhenius form expression (B5) represents a service life characteristic in a power cycle of switching element Qvn (semiconductor chip).

[Expression 3]

$$Nvnf = A \cdot \Delta Tvn^\alpha \cdot \exp\left[\frac{B}{\text{MAX}Tvn + \text{MIN}Tvn}\right] \quad \text{(B5)}$$

Deterioration degree calculating unit 91 calculates a power cycle number Nwnf of an expected service life of switching element Qwn from maximum temperature MAXTwn, minimum temperature MINTwn, and pulsation temperature ΔTwn in one power cycle in accordance with the following Arrhenius form expression (B6). The Arrhenius form expression (B6) represents a service life characteristic in a power cycle of switching element Qwn (semiconductor chip).

[Expression 4]

$$Nwnf = A \cdot \Delta Twn^\alpha \cdot \exp\left[\frac{B}{\text{MAX}Twn + \text{MIN}Twn}\right] \quad \text{(B6)}$$

Herein, A, B, and a are coefficients and determined from an expected service life of a power cycle of switching elements Qun, Qvn, Qwn.

Deterioration degree calculating unit 91 calculates a deterioration degree Run of switching element Qun in one power cycle in accordance with the following expression (B7). Deterioration degree calculating unit 91 calculates a deterioration degree Rvn of switching element Qvn in one power cycle in accordance with the following expression (B8). Deterioration degree calculating unit 91 calculates a deterioration degree Rwn of switching element Qwn in one power cycle in accordance with the following expression (B9).

$$Run = 1/Nunf \quad \text{(B7)}$$

$$Rvn = 1/Nvnf \quad \text{(B8)}$$

$$Rwn = 1/Nwnf \quad \text{(B9)}$$

Deterioration amount calculating unit 92 calculates a deterioration amount Sun of switching element Qun in accordance with the following expression (B10). Deterioration amount calculating unit 92 calculates a deterioration amount Svn of switching element Qvn in accordance with the following expression (B11). Deterioration amount calculating unit 92 calculates a deterioration amount Swn of switching element Qwn in accordance with the following expression (B12).

$$Sun = Sun + Run \quad \text{(B10)}$$

$$Svn = Svn + Rvn \quad \text{(B11)}$$

$$Swn = Swn + Rwn \quad \text{(B12)}$$

Deterioration ratio calculating unit 93 calculates a deterioration ratio Suns of switching element Qun by dividing deterioration amount Sun of switching element Qun by deterioration amount SMAX provided after having reached an expected service life in accordance with the expression (B13). Deterioration ratio calculating unit 93 calculates a deterioration ratio Svns of switching element Qvn by dividing deterioration amount Svn of switching element Qvn by deterioration amount SMAX provided after having reached an expected service life in accordance with the expression (B14). Deterioration ratio calculating unit 93 calculates a deterioration ratio Swns of switching element Qwn by dividing deterioration amount Swn of switching element Qwn by deterioration amount SMAX provided after having reached an expected service life in accordance with the expression (B15). Deterioration ratios Suns, Svns, Swns represent a ratio of a consumed service live with respect to an expected service life of switching elements Qun, Qvn, Qwn.

$$Suns = Sun/S\text{ MAX} \quad \text{(B13)}$$

$$Svns = Svn/S\text{ MAX} \quad \text{(B14)}$$

$$Swns = Swn/S\text{ MAX} \quad \text{(B15)}$$

(Operation of Service Life Diagnosis)

Figure 11:
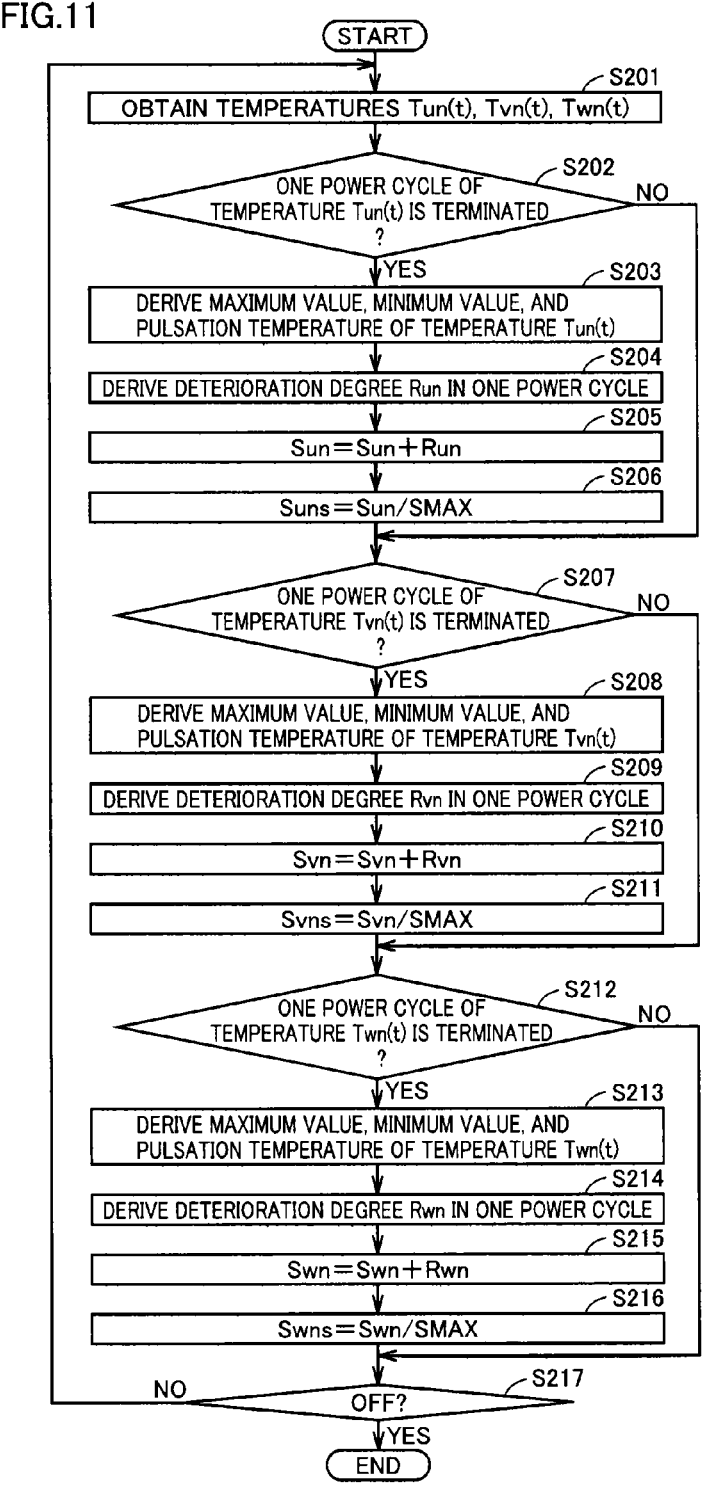
FIG. 11 is a flowchart representing operation procedures for a service life diagnosis of the second embodiment.

FIG. 11 is a flowchart representing operation procedures for the service life diagnosis of the second embodiment.

Referring to FIG. 11, firstly, deterioration degree calculating unit 91 obtains temperatures Tun(t), Tvn(t), Twn(t) (Step S201).

Next, when one power cycle of temperature Tun(t) is terminated (YES in Step S202), deterioration degree calculating unit 91 derives maximum temperature MAXTun, minimum temperature MINTun, and pulsation temperature ΔTun of temperature Tun(t) within one power cycle (Step S203).

Next, deterioration degree calculating unit 91 calculates deterioration degree Run of switching element Qun in one power cycle in accordance with the expressions (B4) and (B7) (Step S204).

Next, deterioration amount calculating unit 92 calculates deterioration amount Sun of switching element Qun in accordance with the expression (B10) (Step S205).

Next, deterioration ratio calculating unit 93 calculates deterioration ratio Suns of switching element Qun in accordance with the expression (B13) (Step S206).

When one power cycle of temperature Tvn(t) is terminated (YES in Step S207), deterioration degree calculating unit 91 derives maximum temperature MAXTvn, minimum temperature MINTvn, and pulsation temperature ΔTvn of temperature Tvn(t) within one power cycle (Step S208).

Next, deterioration degree calculating unit 91 calculates deterioration degree Rvn of switching element Qvn in one power cycle in accordance with the expressions (B5) and (B8) (Step S209).

Next, deterioration amount calculating unit 92 calculates deterioration amount Svn of switching element Qvn in accordance with the expression (B11) (Step S210).

Next, deterioration ratio calculating unit 93 calculates deterioration ratio Svns of switching element Qvn in accordance with the expression (B14) (Step S211).

When one power cycle of temperature Twn(t) is terminated (YES in Step S212), deterioration degree calculating unit 91 derives maximum temperature MAXTwn, minimum temperature MINTwn, and pulsation temperature ΔTwn of temperature Twn(t) within one power cycle (Step S213).

Next, deterioration degree calculating unit 91 calculates deterioration degree Rwn of switching element Qwn in one power cycle in accordance with the expressions (B6) and (B9) (Step S214).

Next, deterioration amount calculating unit 92 calculates deterioration amount Swn of switching element Qwn in accordance with the expression (B12) (Step S215).

Next, deterioration ratio calculating unit 93 calculates deterioration ratio Swns of switching element Qwn in accordance with the expression (B15) (Step S216).

When the power supply is in the on-state (NO in Step S217), the processing from Step S201 is repeated. Moreover, when the power supply is turned off (YES in Step S217), the processing is terminated.

Again, with reference to FIG. 10, external control unit 500 transmits a 2-bit select signal SL through a select terminal PDS.

Output unit 5 outputs a deterioration ratio in accordance with select signal SL per power cycle by following the relationship shown in FIG. 12. When select signal SL is "00," output unit 5 generates a signal setting a maximum value among deterioration ratio Suns, deterioration ratio Svns, and deterioration ratio Swns (in other words, a ratio of the consumed service life with respect to an expected service life of a switching element having a shortest remaining service life) to be an on-pulse or off-pulse duty ratio, and outputs the same from output terminal PD.

When select signal SL is "01," output unit 5 generates a signal setting deterioration ratio Suns of switching element Qun to be an on-pulse or off-pulse duty ratio, and outputs the same from output terminal PD.

When select signal SL is "10," output unit 5 generates a signal setting deterioration ratio Svns of switching element Qvn to be an on-pulse or off-pulse duty ratio, and outputs the same from output terminal PD.

When select signal SL is "11," output unit 5 generates a signal setting deterioration ratio Swns of switching element Qwn to be an on-pulse or off-pulse duty ratio, and outputs the same from output terminal PD.

As described above, according to the present embodiment, similarly to the first embodiment, the number of A/D converters and insulating elements can be reduced, so that the service life diagnosis can be performed in a small circuit configuration. Consequently, increase in size of the power module can be prevented. Moreover, by detecting the temperatures in the periphery of all three elements of the lower arms, the service life diagnosis with a higher accuracy can be performed. The temperature in the periphery of elements of the lower arms rather than the temperature in the periphery of the elements of the upper arms are detected as described above because the elements of the lower arms have less change in the voltage, and a noise is less likely to be added to the temperature sensor.

Modified Example 1 of Second Embodiment

Output unit 5 generates a serial signal including a start bit, a deterioration ratio (b0 to b5), and stop bits per power cycle as shown in FIG. 7, and outputs the same from output terminal PD.

When select signal SL is "00," output unit 5 generates a serial signal including a start bit, a maximum value (6-bit) among deterioration ratio Suns, deterioration ratio Svns, and deterioration ratio Swns (in other words, a ratio of a consumed service life with respect to an expected service life of a switching element having a shortest remaining service life), and stop bits, and outputs the same from output terminal PD.

When select signal SL is "01," output unit 5 generates a serial signal including a start bit, 6-bit deterioration ratio Suns, and stop bits, and outputs the same from output terminal PD. When select signal SL is "10," output unit 5 generates a serial signal including a start bit, 6-bit deterioration ratio Svns, and stop bits, and outputs the same from output terminal PD. When select signal SL is "11," output unit 5 generates a serial signal including a start bit, 6-bit deterioration ratio Swns, and stop bits, and outputs the same from output terminal PD.

It should be noted that, although the deterioration ratio is expressed by 6-bits in the modified example described above, this is one example, and the deterioration ratio may be expressed by n-bits (n is a natural number greater than or equal to 1).

Modified Example 2 of Second Embodiment

Figure 13:
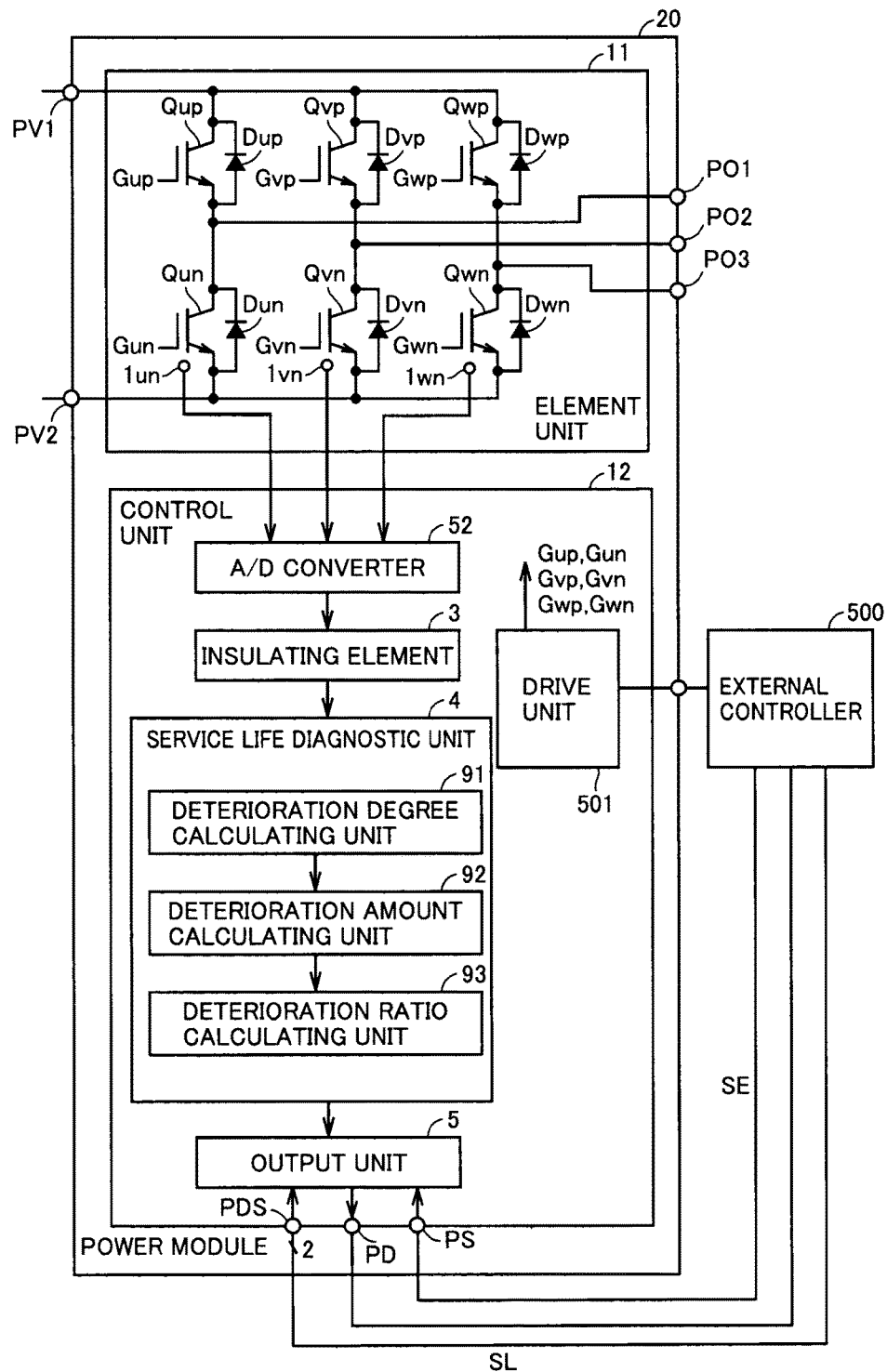
FIG. 13 represents a configuration of a power module of a modified example 2 of the second embodiment.

FIG. 13 represents a configuration of a power module of a modified example 2 of the second embodiment.

This power module 20 includes a select terminal PS.

External control unit 500 transmits 1-bit select signal SE through select terminal PS. Select signal SE is a signal which designates if output unit 5 outputs a diagnostic result in an analog method described in the second embodiment or outputs a diagnostic result in a digital method described in modified example 1 of the second embodiment.

When select signal SE is "1," and select signal SL is "00," output unit 5 generates a signal setting a maximum value among deterioration ratio Suns, deterioration ratio Svns, and deterioration ratio Swns (in other words, a ratio of a consumed service life with respect to an expected service life of a switching element having a shortest remaining service life) to be an on-pulse or off-pulse duty ratio, and outputs the same from output terminal PD.

When select signal SE is "1," and select signal SL is "01," output unit 5 generates a signal setting deterioration ratio Suns of switching element Qun to be an on-pulse or off-pulse duty ratio, and outputs the same from output terminal PD.

When select signal SE is "1," and select signal SL is "10," output unit 5 generates a signal setting deterioration ratio Svns of switching element Qvn to be an on-pulse or off-pulse duty ratio, and outputs the same from output terminal PD.

When select signal SE is "1," and select signal SL is "11," output unit 5 generates a signal setting deterioration ratio Swns of switching element Qwn to be an on-pulse or off-pulse duty ratio, and outputs the same from output terminal PD.

When select signal SE is "0," and select signal SL is "00," output unit 5 generates a serial signal including a start bit, a maximum value (6-bit) among deterioration ratio Suns, deterioration ratio Svns, and deterioration ratio Swns (in other words, a ratio of a consumed service life with respect to an expected service life of a switching element having a shortest remaining service life), and stop bits, and outputs the same from output terminal PD.

When select signal SE is "0," and select signal SL is "01," output unit 5 generates a serial signal including a start bit, 6-bit deterioration ratio Suns, and stop bits, and outputs the same from output terminal PD.

When select signal SE is "0," and select signal SL is "10," output unit 5 generates a serial signal including a start bit, 6-bit deterioration ratio Svns, and stop bits, and outputs the same from output terminal PD.

When select signal SE is "0," and select signal SL is "11," output unit 5 generates a serial signal including a start bit, 6-bit deterioration ratio Swns, and stop bits, and outputs the same from output terminal PD.

It should be noted that, although the deterioration ratio is expressed by 6-bits in the modified example described above, this is one example, and the deterioration ratio may be expressed by n-bits (n is a natural number greater than or equal to 1).

Modified Example 3 of Second Embodiment

Figure 14:
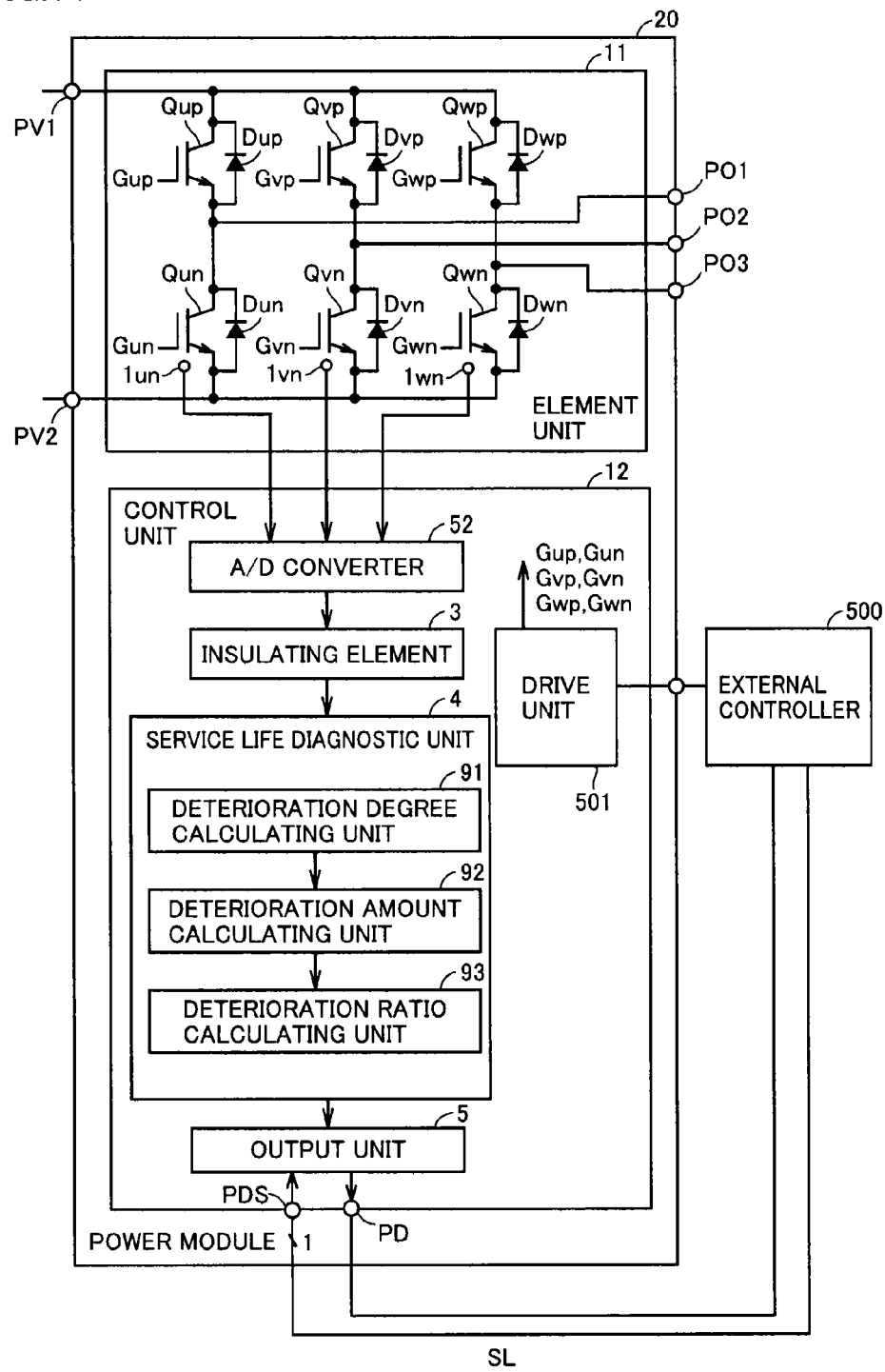
FIG. 14 represents a configuration of a power module of a modified example 3 of the second embodiment.

FIG. 14 represents a configuration of a power module of modified example 3 of the second embodiment.

Figure 15:
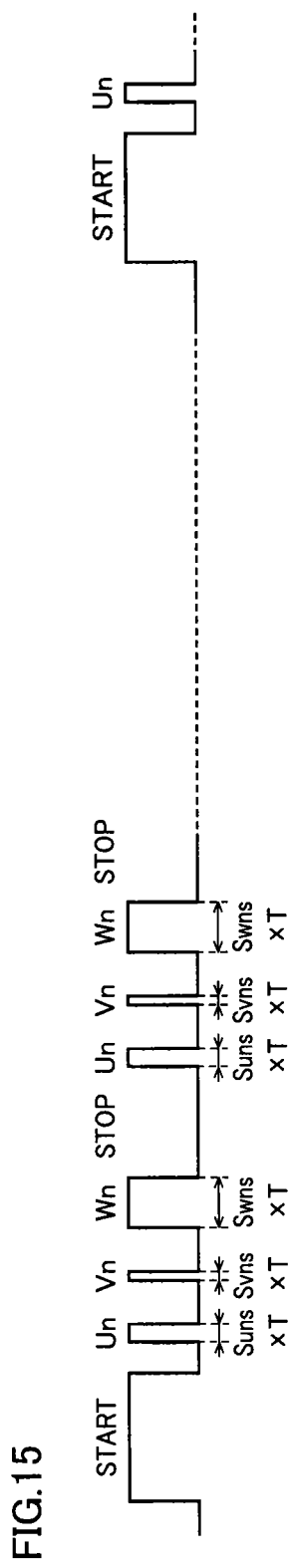
FIG. 15 represents an example of a signal outputted from an output terminal PD in a modified example 3 of the second embodiment.

FIG. 15 represents an example of a signal outputted from output terminal PD in modified example 3 of the second embodiment.

External control unit 500 transmits 1-bit select signal SL through select terminal PDS.

When select signal SL is "0," output unit 5 generates a signal setting a maximum value among deterioration ratio Suns, deterioration ratio Svns, and deterioration ratio Swns (in other words, a ratio of a consumed service life with respect to an expected service life of a switching element having a shortest remaining service life) to be an on-pulse duty ratio, and outputs the same from output terminal PD.

When select signal SL is "1," output unit 5 of the present modified example, as shown in FIG. 15, includes START (the "H" level continues) and STOP (the "L" level continues), generates a signal setting deterioration ratio Suns of switching element Qun to be a first on-pulse duty ratio, deterioration ratio Svns of switching element Qvn to be a second on-pulse duty ratio, and deterioration ratio Swns of switching element Qwn to be a third on-pulse duty ratio, and outputs the same from output terminal PD.

It should be noted that, instead of representing deterioration ratios Suns, Svns, Swns and a maximum value of those with an on-pulse duty ratio, it may be represented by an off-pulse duty ratio.

Modified Example 4 of Second Embodiment

Figure 16:
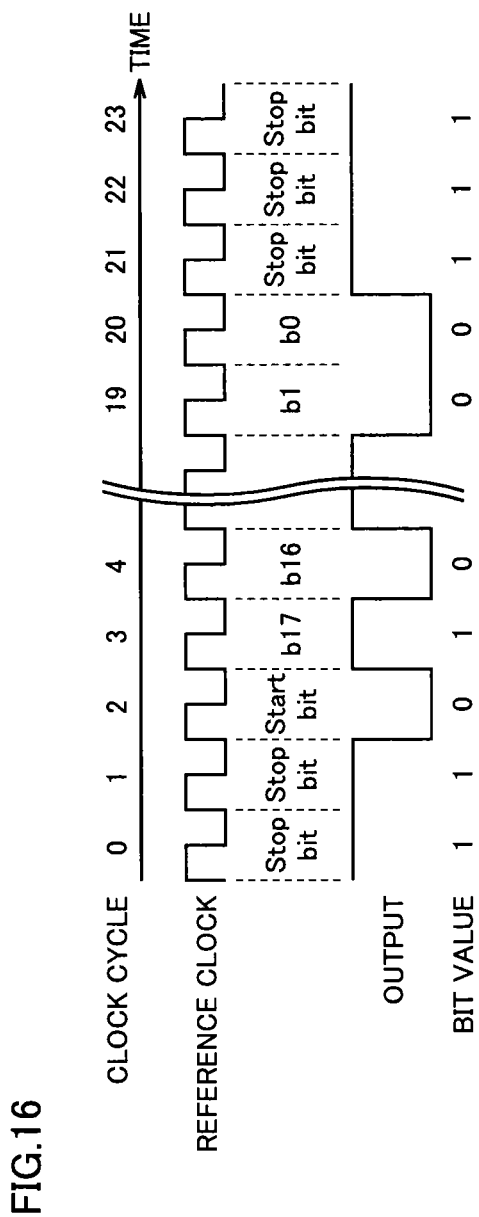
FIG. 16 represents an example of a signal outputted from an output terminal PD in the case where a select signal SL is "1" in a modified example 4 of the second embodiment.

FIG. 16 represents an example of a signal outputted from output terminal PD when select signal SL is "1" in a modified example 4 of the second embodiment.

When select signal SL is "0," output unit 5, generates a serial signal including a start bit, a maximum value (6-bit) among deterioration ratio Suns, deterioration ratio Svns, and deterioration ratio Swns (in other words, a ratio of a consumed service life with respect to an expected service life of a switching element having a shortest remaining service life), and stop bits as shown in FIG. 7, and outputs the same from output terminal PD.

When select signal SL is "1," output unit 5 generates a serial signal including a start bit, deterioration ratio suns (b12 to b17), deterioration ratio Svns (b6 to b11), deterioration ratio Swns (b0 to b5), and stop bits as shown in FIG. 16, and outputs the same from output terminal PD.

It should be noted that, although the deterioration ratio is expressed by 6-bits in the modified example described above, this is one example, and the deterioration ratio may be expressed by n-bits (n is a natural number greater than or equal to 1).

Modified Example 5 of Second Embodiment

Figure 17:
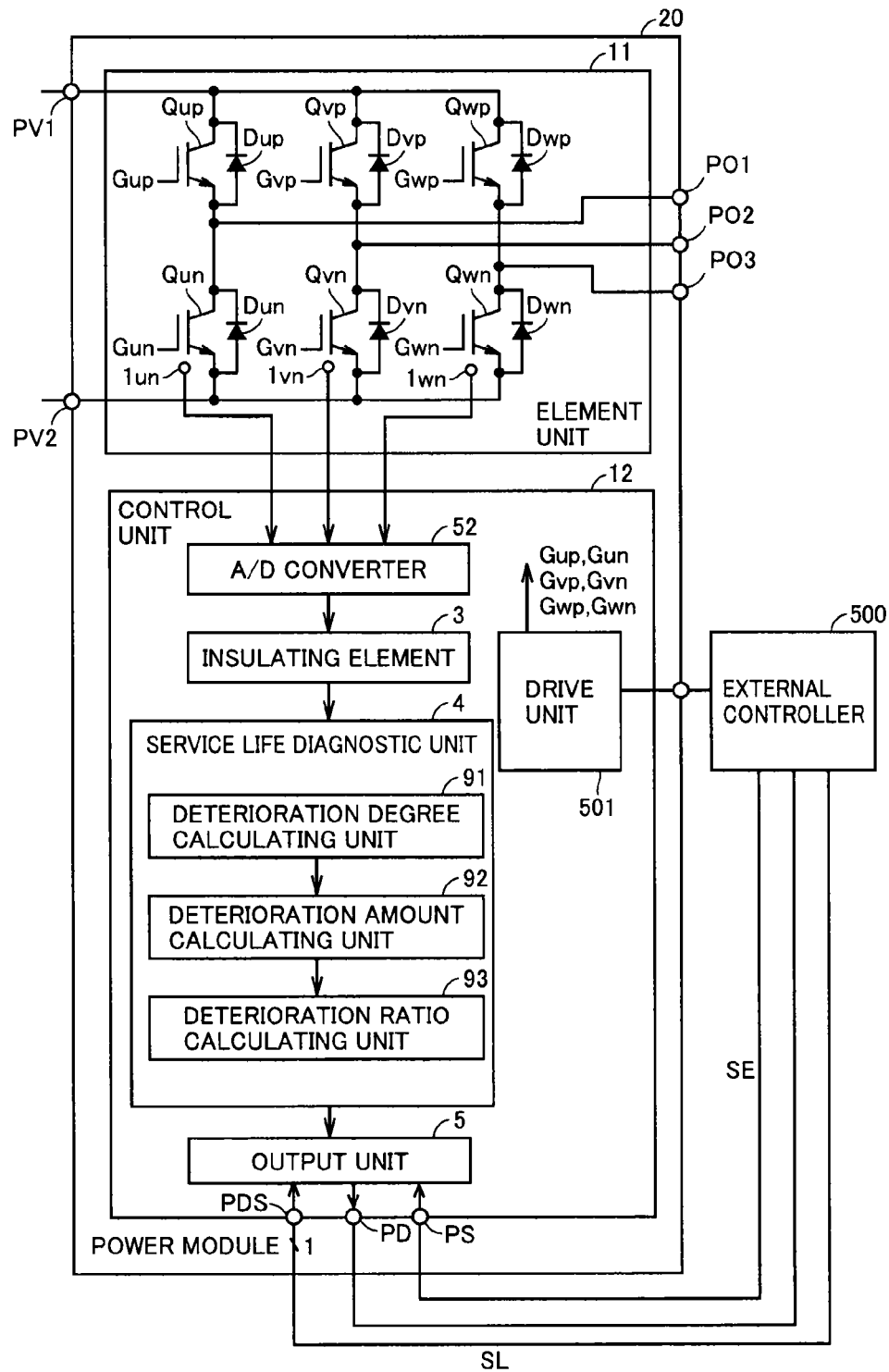
FIG. 17 represents a configuration of a power module of a modified example 5 of the second embodiment.

FIG. 17 represents a configuration of a power module of a modified example 5 of the second embodiment.

This power module 20 includes select terminal PS.

External control unit 500 sends 1-bit select signal SE through select terminal PS. Select signal SE is a signal which designates if output unit 5 outputs a diagnostic result in an analog method described in modified example 3 of the second embodiment or outputs a diagnostic result in a digital method described in modified example 4 of the second embodiment.

When select signal SE is "1," and select signal SL is "0," output unit 5, similarly to modified example 3 of the second embodiment, generates a signal setting a maximum value among deterioration ratio Suns, deterioration ratio Svns, and deterioration ratio Swns (in other words, a ratio of a consumed service life with respect to an expected service life of a switching element having a shortest remaining service life) to be an on-pulse or off-pulse duty ratio, and outputs the same from output terminal PD.

When select signal SE is "1," and select signal SL is "1," output unit 5 includes START (the "H" level continues) and STOP (the "L" level continues), generates a signal setting deterioration ratio Suns of switching element Qun to be a first on-pulse or off-pulse duty ratio, deterioration ratio Svns of switching element Qvn to be a second on-pulse or off-pulse duty ratio, and deterioration ratio Swns of switching element Qwn to be a third on-pulse or off-pulse duty ratio, and outputs the same from output terminal PD.

When select signal SE is "0," and select signal SL is "0," output unit 5 generates a serial signal including a start bit, a maximum value (6-bit) among deterioration ratio Suns, deterioration ratio Svns, and deterioration ratio Swns (in other words, a ratio of a consumed service life with respect to an expected service life of a switching element having a shortest remaining service life), and stop bits, and outputs the same from output terminal PD.

When select signal SE is "0," and select signal SL is "1," output unit 5 generates a serial signal including a start bit, deterioration ratio suns (b12 to b17), deterioration ratio Svns (b6 to b11), deterioration ratio Swns (b0 to b5), and stop bits, and outputs the same from output terminal PD.

It should be noted that, although the deterioration ratio is expressed by 6-bits in the modified example described above, this is one example, and the deterioration ratio may be expressed by n-bits (n is a natural number greater than or equal to 1).

Modified Example 6 of Second Embodiment

Figure 18:
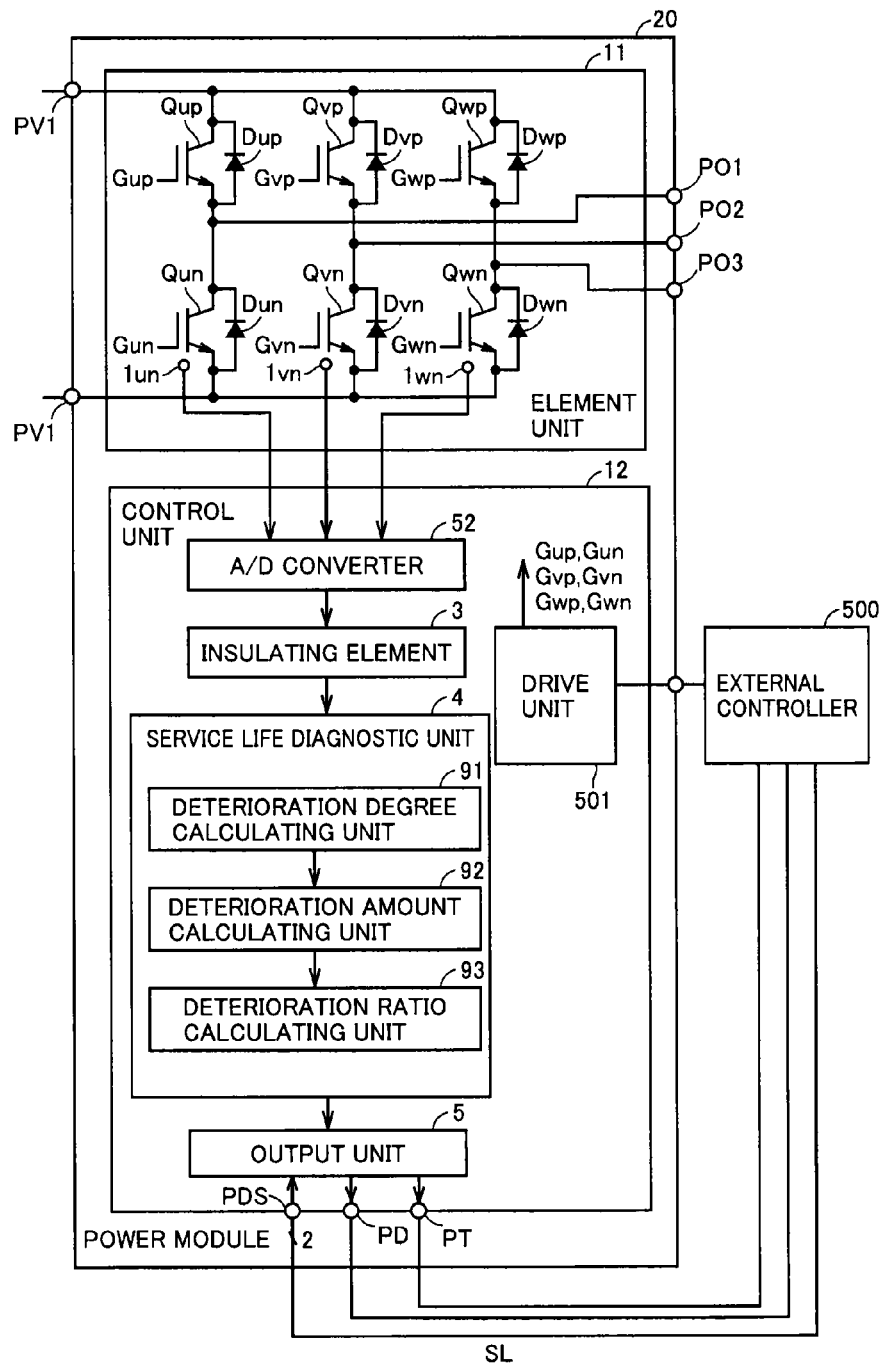
FIG. 18 represents a configuration of a power module of a modified example 6 of the second embodiment.

FIG. 18 represents a configuration of a power module of a modified example 6 of the second embodiment.

This power module 20 includes output terminal PT.

Output unit 5 generates a serial signal including a start bit, 6-bit maximum temperature MAXTun, 6-bit minimum temperature MINTun, 6-bit pulsation temperature $\Delta$Tun, 6-bit maximum temperature MAXTvn, 6-bit minimum temperature MINTvn, 6-bit pulsation temperature $\Delta$Tvn, 6-bit maximum temperature MAXTwn, G-bit minimum temperature MINTwn, 6-bit pulsation temperature $\Delta$Twn, and stop bits per power cycle, and outputs the same from output terminal PT.

It should be noted that output unit 5 may output some of the nine temperatures described above from output terminal PT. Moreover, output unit 5 may output an average of maximum temperature MAXTun and minimum temperature MINTun, an average of maximum temperature MAXTvn and minimum temperature MINTvn, and an average of maximum temperature MAXTwn and minimum temperature MINTwn per power cycle.

It should be noted that, although the temperature is represented by 6-bits in the modified example described above, this is one example, and the temperature may be represented by n-bits (n is a natural number greater than or equal to 1).

Third Embodiment

Figure 19:
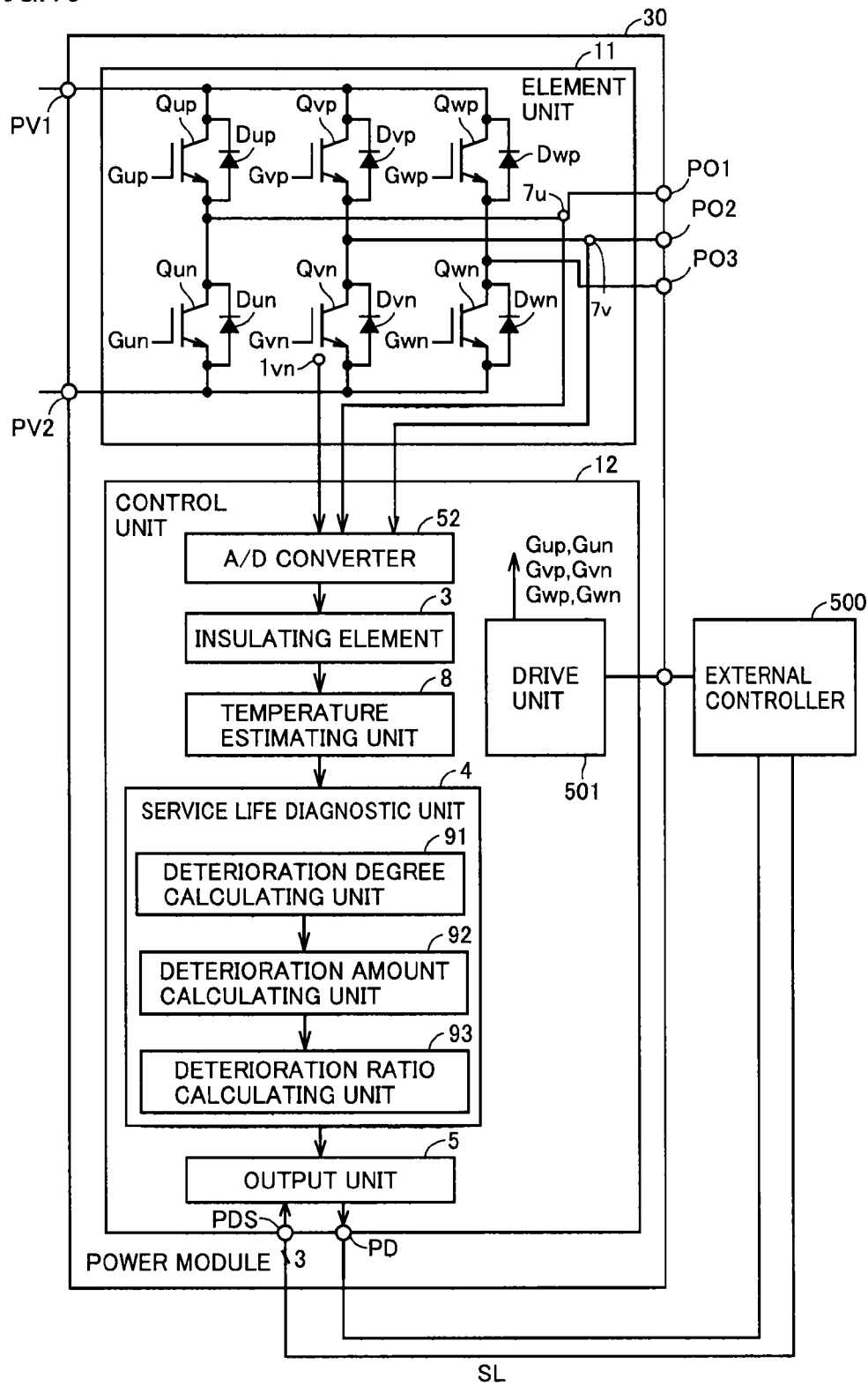
FIG. 19 represents a configuration of a power module of a third embodiment.

FIG. 19 represents a configuration of a power module of a third embodiment.

A power module 30 of FIG. 19 includes current sensors 7u, 7v and a temperature estimating unit 8 which are not included in the power module of FIG. 1.

Current sensor 7u detects a magnitude of a U-phase output current of power module 30. Current sensor 7v detects a magnitude of a V-phase output current of power module 30.

A/D converter 52 converts an analog signal representing a temperature transmitted from temperature sensor 1un into a digital signal. A/D converter 52 converts an analog signal representing a U-phase current transmitted from current sensor 7u into a digital signal. A/D converter 52 converts an analog signal representing a V-phase current transmitted from current sensor 7v into a digital signal.

A/D converter 52 has three input channels and one output channel. By sequentially designating input channels subjected to A/D conversion, signals from temperature sensor 1un and current sensors 7u, 7v are converted into digital signals.

A digital signal Tvn(t) representing a temperature, a digital signal Iu(t) representing a U-phase current, and a digital signal Iv(t) representing a V-phase current outputted from A/D converter 52 are transmitted to temperature estimating unit 8 through insulating element 3.

Temperature estimating unit 8 derives a W-phase current Iw(t) from U-phase current Iu(t) and V-phase current Iv(t) in accordance with the following Kirchhoff expression (C1).

$$Iw = -Iu - Iv \quad (C1)$$

Temperature estimating unit 8 calculates a calorific value Hup of switching element Qup, a calorific value Hvp of switching element Qvp, a calorific value Hwp of switching element Qwp, a calorific value Hun of switching element Qun, a calorific value Hvn of switching element Qvn, and a calorific value Hwn of switching element Qwn per temperature calculation cycle Δt in accordance with the expressions (C2) to (C31). Herein, t1 represents a start time of the temperature calculation cycle, and t2 represents an end time of the temperature calculation cycle.

$$Iup = Iu \ (Iu \geq 0, \text{ and } Qup \text{ is in the on-state}) \quad (C2)$$

$$Iup = 0 \ (Iu < 0, \text{ or } Qup \text{ is in the off-state}) \quad (C3)$$

[Expression 5]

$$Hcup = \int_{t1}^{t2} Iup \cdot Vce \, dt \quad (C4)$$

$$Hsup = fs * Js \quad (C5)$$

$$Hup = Hcup + Hsup \quad (C6)$$

$$Ivp = Iv \ (Iv \geq 0, \text{ and } Qvp \text{ is in the on-state}) \quad (C7)$$

$$Ivp = 0 \ (Iv < 0, \text{ or } Qvp \text{ is in the off-state}) \quad (C8)$$

[Expression 6]

$$Hcvp = \int_{t1}^{t2} Ivp \cdot Vce \, dt \quad (C9)$$

$$Hsvp = fs * Js \quad (C10)$$

$$Hvp = Hcvp + Hsvp \quad (C11)$$

$$Iwp = Iw \ (Iw \geq 0, \text{ and } Qwp \text{ is in the on-state}) \quad (C12)$$

$$Iwp = 0 \ (Iw < 0, \text{ or } Qwp \text{ is in the off-state}) \quad (C13)$$

[Expression 7]

$$Hcwp = \int_{t1}^{t2} Iwp \cdot Vce \, dt \quad (C14)$$

$$Hswp = fs * Js \quad (C15)$$

$$Hwp = Hcwp + Hswp \quad (C16)$$

$$Iun = Iu \ (Iu \geq 0, \text{ and } Qun \text{ is in the on-state}) \quad (C17)$$

$$Iun = 0 \ (Iu < 0, \text{ or } Qnn \text{ is in the off-state}) \quad (C18)$$

[Expression 8]

$$Hcun = \int_{t1}^{t2} Iun \cdot Vce \, dt \quad (C19)$$

$$Hsun = fs * Js \quad (C20)$$

$$Hun = Hcun + Hsun \quad (C21)$$

$$Ivn = Iv \ (Iv \geq 0, \text{ and } Qvn \text{ is in the on-state}) \quad (C22)$$

$$Ivn = 0 \ (Iv < 0, \text{ or } Qvn \text{ is in the off-state}) \quad (C23)$$

[Expression 9]

$$Hcvn = \int_{t1}^{t2} Ivn \cdot Vce \, dt \quad (C24)$$

$$Hsvn = fs * Js \quad (C25)$$

$$Hvn = Hcvn + Hsvn \quad (C26)$$

$$Iwn = Iw \ (Iw \geq 0, \text{ and } Qwn \text{ is in the on-state}) \quad (C27)$$

$$Iwn = 0 \ (Iw < 0, \text{ or } Qwn \text{ is in the off-state}) \quad (C28)$$

[Expression 10]

$$Hcwn = \int_{t1}^{t2} Iwn \cdot Vce \, dt \quad (C29)$$

$$Hswn = fs * Js \quad (C30)$$

$$Hwn = Hcwn + Hswn \quad (C31)$$

In the expressions (C2) to (C31), the items Iup(t), Ivp(t), Iwp(t), Iun(t), Ivn(t), Iwn(t) represent a current flowing to switching element Qup, a current flowing to switching element Qvp, a current flowing to switching element Qwp, a current flowing to switching element Qun, a current flowing to switching element Qvn, and a current flowing to switching element Qwn, respectively.

The items Hcup, Hcvp, Hcwp, Hcun, Hcvn, Hcwn are calorific values of a conduction loss, and the items Hsup, Hsvp, Hswp, Hsun, Hsvn, Hswn are calorific values of a switching loss. The item Vice is a saturation voltage of switching elements Qup, Qvp, Qwp, Qun, Qvn, Qwn. The item fs is a switching frequency of switching element Qup, Qvp, Qwp, Qun, Qvn, Qwn within temperature calculation cycle Δt, and can be calculated with use of switching frequency fc of switching elements Qup, Qvp, Qwp, Qun, Qvn, Qwn. The item js is a loss due to one switching of switching elements Qup, Qvp, Qwp, Qun, Qvn, Qwn. The item t1–t2 is temperature calculation cycle Δt.

Temperature estimating unit 8 calculates a base temperature Tb per temperature calculation cycle Δt in accordance with the expression (C32).

[Expression 11]

$$Tb = Tvn - Rth \frac{1}{\Delta t} \int_{t1}^{t2} Hvn \, dt \qquad (C32)$$

Herein, the item Rth is a thermal resistance between the chip and the case.

Temperature estimating unit 8 calculates temperatures Tup, Tun, Tvp, Twp, Twn in accordance with the expressions (C33) to (C37).

[Expression 12]

$$Tup = Tb + Rth \frac{1}{\Delta t} \int_{t1}^{t2} Hup \, dt \qquad (C33)$$

$$Tvp = Tb + Rth \frac{1}{\Delta t} \int_{t1}^{t2} Hvp \, dt \qquad (C34)$$

$$Twp = Tb + Rth \frac{1}{\Delta t} \int_{t1}^{t2} Hwp \, dt \qquad (C35)$$

$$Tun = Tb + Rth \frac{1}{\Delta t} \int_{t1}^{t2} Hun \, dt \qquad (C36)$$

$$Twn = Tb + Rth \frac{1}{\Delta t} \int_{t1}^{t2} Hwn \, dt \qquad (C37)$$

Deterioration degree calculating unit 91 derives maximum temperature MAXTup and minimum temperature MINTup in one power cycle from temperature Tup per temperature calculation cycle Δt within one power cycle. Further, deterioration degree calculating unit 91 calculates a difference between maximum temperature MAXTup and minimum temperature MINTup to derive pulsation temperature ΔTup in one power cycle.

$$\Delta Tup = \text{MAX } Tup - \text{MIN } Tup \qquad (D1)$$

Deterioration degree calculating unit 91 derives maximum temperature MAXTvp and minimum temperature MINTvp in one power cycle from temperature Tvp(t) per temperature calculation cycle Δt within one power cycle. Further, deterioration degree calculating unit 91 calculates a difference between maximum temperature MAXTvp and minimum temperature MINTvp to derive pulsation temperature ΔTvp in one power cycle.

$$\Delta Tvp = \text{MAX } Tvp - \text{MIN } Tvp \qquad (D2)$$

Deterioration degree calculating unit 91 derives maximum temperature MAXTwp and minimum temperature MINTwp in one power cycle from temperature Twp(t) per temperature calculation cycle Δt within one power cycle. Further, deterioration degree calculating unit 91 calculates a difference between maximum temperature MAXTwp and minimum temperature MINTwp to derive pulsation temperature ΔTwp in one power cycle.

$$\Delta Twp = \text{MAX } Twp - \text{MIN } Twp \qquad (D3)$$

Deterioration degree calculating unit 91 derives maximum temperature MAXTun and minimum temperature MINTun in one power cycle from temperature Tun(t) per temperature calculation cycle Δt within one power cycle. Further, deterioration degree calculating unit 91 calculates a difference between maximum temperature MAXTun and minimum temperature MINTun to derive pulsation temperature ΔTun in one power cycle.

$$\Delta Tun = \text{MAX } Tun - \text{MIN } Tun \qquad (D4)$$

Deterioration degree calculating unit 91 derives maximum temperature MAXTvn and minimum temperature MINTvn in one power cycle from temperature Tvn(t) per temperature calculation cycle Δt within one power cycle. Further, deterioration degree calculating unit 91 calculates a difference between maximum temperature MAXTvn and minimum temperature MINTvn to derive pulsation temperature ΔTvn in one power cycle.

$$\Delta Tvn = \text{MAX } Tvn - \text{MIN } Tvn \qquad (D5)$$

Deterioration degree calculating unit 91 derives maximum temperature MAXTwn and minimum temperature MINTwn in one power cycle from temperature Twn(t) per temperature calculation cycle Δt within one power cycle. Further, deterioration degree calculating unit 91 calculates a difference between maximum temperature MAXTwn and minimum temperature MINTwn to derive pulsation temperature ΔTwn in one cycle.

$$\Delta Twn = \text{MAX } Twn - \text{MIN } Twn \qquad (D6)$$

Deterioration degree calculating unit 91 calculates a power cycle number Nupf of an expected service life of switching element Qup from maximum temperature MAXTup, minimum temperature MINTup, and pulsation temperature ΔTup in one power cycle in accordance with the following Arrhenius form expression (D7). The Arrhenius form expression (D7) represents a service life characteristic in a power cycle of switching element Qup (semiconductor chip).

[Expression 13]

$$Nupf = A \cdot \Delta Tup^\alpha \cdot \exp\left[\frac{B}{\text{MAX}Tup + \text{MIN}Tup}\right] \qquad (D7)$$

Deterioration degree calculating unit 91 calculates a power cycle number Nvpf of an expected service life of switching element Qvp from maximum temperature MAXTvp, minimum temperature MINTvp, and pulsation temperature ΔTvp in one power cycle in accordance with the following Arrhenius form expression (D8). The Arrhenius form expression (D8) represents a service life characteristic in a power cycle of switching element Qvp (semiconductor chip).

[Expression 14]

$$Mvpf = A \cdot \Delta Tvp^\alpha \cdot \exp\left[\frac{B}{\text{MAX}Tvp + \text{MIN}Tvp}\right] \qquad (D8)$$

Deterioration degree calculating unit 91 calculates a power cycle number Nwpf of an expected service life of switching element Qwp from maximum temperature MAXTwp, minimum temperature MINTwp, and pulsation temperature ΔTwp in one power cycle in accordance with the following Arrhenius form expression (D9). The Arrhenius form expression (D9) represents a service life characteristic in a power cycle of switching element Qwp (semiconductor chip).

[Expression 15]

$$Nwpf = A \cdot \Delta Twp^\alpha \cdot \exp\left[\frac{B}{\text{MAX}Twp + \text{MIN}Twp}\right] \qquad (D9)$$

Deterioration degree calculating unit 91 calculates a power cycle number Nunf of an expected service life of switching element Qun from maximum temperature MAXTun, minimum temperature MINTun, and pulsation temperature ΔTun in one power cycle in accordance with the following Arrhenius form expression (D10). The Arrhenius form expression (D10) represents a service life characteristic in a power cycle of switching element Qun (semiconductor chip).

[Expression 16]

$$Nunf = A \cdot \Delta Tun^{\alpha} \cdot \exp\left[\frac{B}{\text{MAX}Tun + \text{MIN}Tun}\right] \quad \text{(D10)}$$

Deterioration degree calculating unit 91 calculates a power cycle number Nvnf of an expected service life of switching element Qvn from maximum temperature MAXTvn, minimum temperature MINTvn, and pulsation temperature ΔTvn in one power cycle in accordance with the following Arrhenius form expression (D11). The Arrhenius form expression (D11) represents a service life characteristic in a power cycle of switching element Qvn (semiconductor chip).

[Expression 17]

$$Nvnf = A \cdot \Delta Tvn^{\alpha} \cdot \exp\left[\frac{B}{\text{MAX}Tvn + \text{MIN}Tvn}\right] \quad \text{(D11)}$$

Deterioration degree calculating unit 91 calculates a power cycle number Nwnf of an expected service life of switching element Qwn from maximum temperature MAXTwn, minimum temperature MINTwn, and pulsation temperature ΔTwn in one power cycle in accordance with the following Arrhenius form expression (D12). The Arrhenius form expression (D12) represents a service life characteristic in a power cycle of switching element Qwn (semiconductor chip).

[Expression 18]

$$Nwnf = A \cdot \Delta Twn^{\alpha} \cdot \exp\left[\frac{B}{\text{MAX}Twn + \text{MIN}Twn}\right] \quad \text{(D12)}$$

Herein, A, B, and α are coefficients and determined from an expected service life of a power cycle of switching elements Qup, Qvp, Qwp, Qun, Qvn, Qwn.

Deterioration degree calculating unit 91 calculates deterioration degree Rup of switching element Qup, deterioration degree Rvp of switching element Qvp, deterioration degree Rwp of switching element Qwp, deterioration degree Run of switching element Qun, deterioration degree Rvn of switching element Qvn, deterioration degree Rwn of switching element Qwn in one power cycle in accordance with the following expressions (D13) to (D18).

$$Rup = 1/Nupf \quad \text{(D13)}$$

$$Rvp = 1/Nvpf \quad \text{(D14)}$$

$$Rwp = 1/Nwpf \quad \text{(D15)}$$

$$Run = 1/Nunf \quad \text{(D16)}$$

$$Rvn = 1/Nvnf \quad \text{(D17)}$$

$$Rwn = 1/Nwnf \quad \text{(D18)}$$

Deterioration amount calculating unit 92 calculates deterioration amount Sup of switching element Qup, deterioration amount Svp of switching element Qvp, deterioration amount Swp of switching element Qwp, deterioration amount Sun of switching element Qun, deterioration amount Svn of switching element Qvn, and deterioration amount Swn of switching element Qwn in accordance with the following expressions (D19) to (D24).

$$Sup = Sup + Rup \quad \text{(D19)}$$

$$Svp = Svp + Rvp \quad \text{(D20)}$$

$$Swp = Swp + Rwp \quad \text{(D21)}$$

$$Sun = Sun + Run \quad \text{(D22)}$$

$$Svn = Svn + Rvn \quad \text{(D23)}$$

$$Swn = Swn + Rwn \quad \text{(D24)}$$

Deterioration ratio calculating unit 93 divides deterioration amount Sup of switching element Qup, deterioration amount Svp of switching element Qvp, deterioration amount Swp of switching element Qwp, deterioration amount Sun of switching element Qun, deterioration amount Svn of switching element Qvn, and deterioration amount Swn of switching element Qwn respectively by deterioration amounts SMAX provided after having reached an expected service life in accordance with the expressions (D25) to (D30) to calculate deterioration ratio Sups of switching element Qup, deterioration ratio Svps of switching element Qvp, deterioration ratio Swps of switching element Qwp, deterioration ratio Suns of switching element Qun, deterioration ratio Svns of switching element Qvn, and deterioration ratio Swns of switching element Qwn.

$$Sups = Sup/S \text{ MAX} \quad \text{(D25)}$$

$$Svps = Svp/S \text{ MAX} \quad \text{(D26)}$$

$$Swps = Swp/S \text{ MAX} \quad \text{(D27)}$$

$$Suns = Sun/S \text{ MAX} \quad \text{(D28)}$$

$$Svns = Svn/S \text{ MAX} \quad \text{(D29)}$$

$$Swns = Swn/S \text{ MAX} \quad \text{(D30)}$$

(Operation of Service Life Diagnosis)

Figure 20:
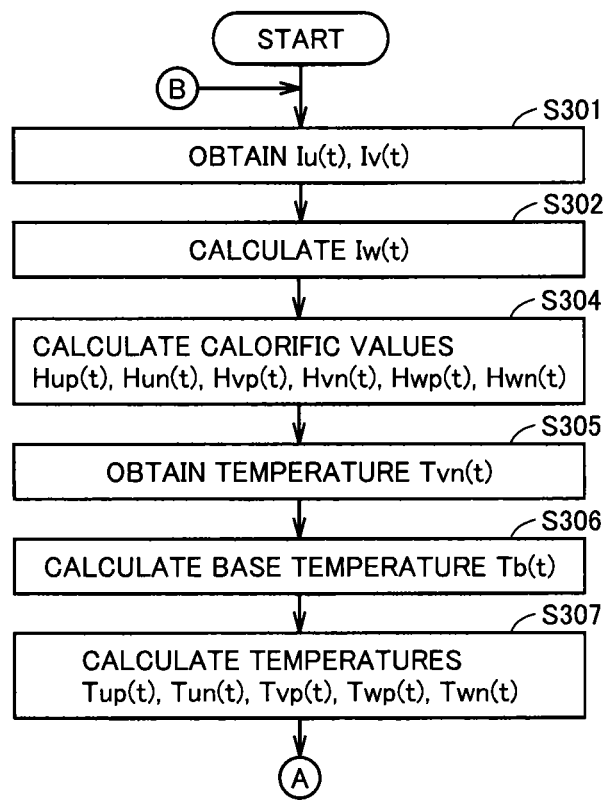
FIG. 20 is a flowchart representing operation procedures for a service life diagnosis of the third embodiment.
Figure 21:
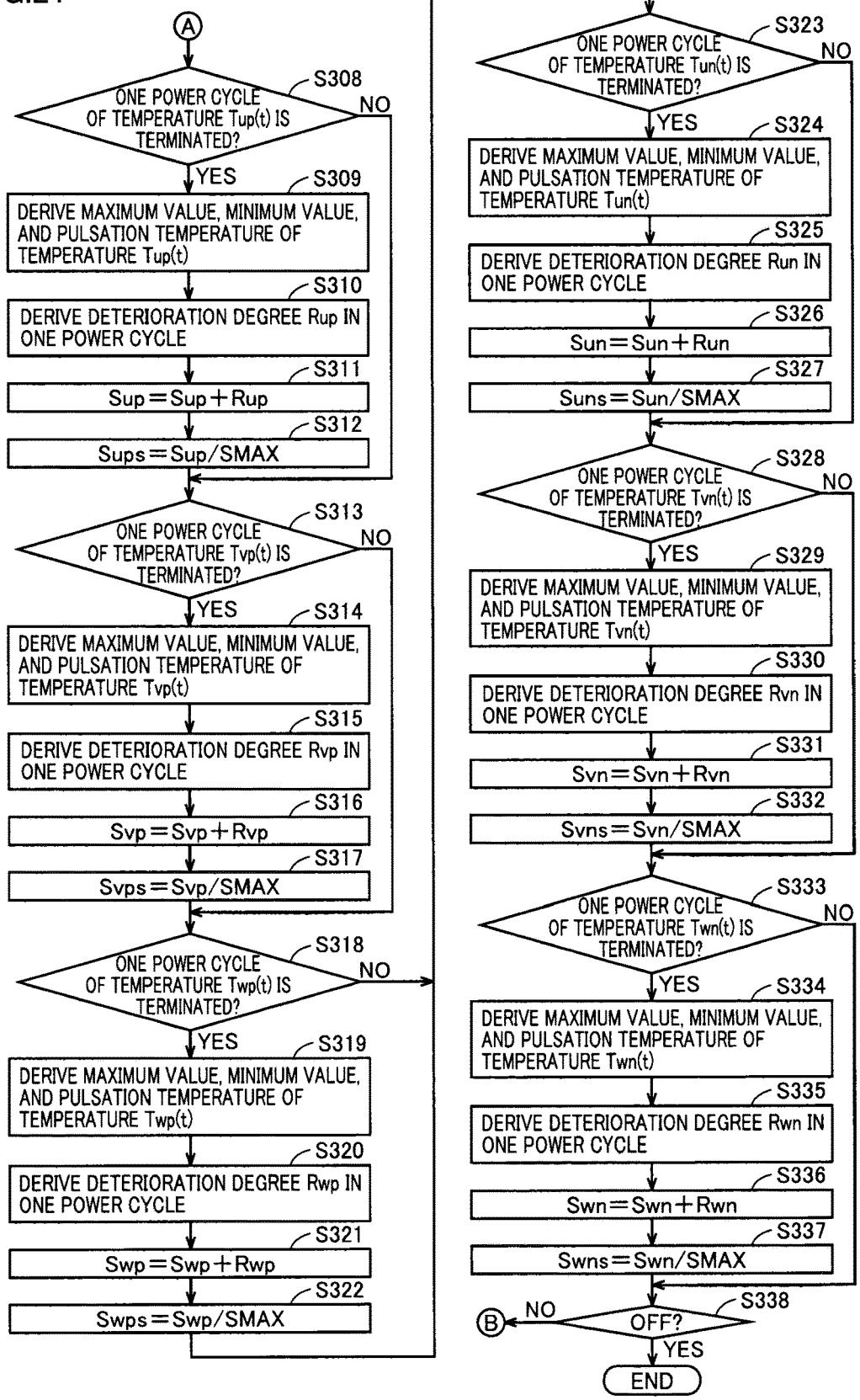
FIG. 21 is a flowchart representing operation procedures for a service life diagnosis of the third embodiment.

FIGS. 20 and 21 are flowcharts representing operation procedures for the service life diagnosis of the third embodiment.

Referring to FIGS. 20 and 21, temperature estimating unit 8 obtains U-phase current Iu(t) and V-phase current Iv(t) (Step S301).

Next, temperature estimating unit 8 derives W-phase current Iw(t) in accordance with the expression (C1) (Step S302).

Next, temperature estimating unit 8 calculates calorific value Hup of switching element Qup, calorific value Hvp of switching element Qvp, calorific value Hwp of switching element Qwp, calorific value Hun of switching element Qun, calorific value Hvn of switching element Qvn, and calorific value Hwn of switching element Qwn per temperature calculation cycle Δt in accordance with the expressions (C2) to (C31) (Step S304).

Next, temperature estimating unit 8 obtains temperature Tvn(t) per temperature calculation cycle Δt (Step S305).

Next, temperature estimating unit 8 calculates base temperature Tb per temperature calculation cycle Δt in accordance with the expression (C32) (Step S306).

Next, temperature estimating unit 8 calculates temperatures Tup(t), Tun(t), Tvp(t), Twp(t), Twn(t) per calculation cycle Δt in accordance with the expressions (C33) to (C37) (Step S307).

When one power cycle of temperature Tup(t) is terminated (YES in Step S308), deterioration degree calculating unit 91 derives maximum temperature MAXTup, minimum temperature MINTup, and pulsation temperature ΔTup of temperature Tup(t) within one power cycle (Step S309).

Next, deterioration degree calculating unit 91 calculates deterioration degree Rup of switching element Qup in one power cycle in accordance with the expressions (D7) and (D13) (Step S310).

Next, deterioration amount calculating unit 92 calculates deterioration amount Sup of switching element Qup in accordance with the expression (D19) (Step S311).

Next, deterioration ratio calculating unit 93 calculates deterioration ratio Sups of switching element Qup in accordance with the expression (D25) (Step S312).

When one power cycle of temperature Tvp(t) is terminated (YES in Step S313), deterioration degree calculating unit 91 derives maximum temperature MAXTvp, minimum temperature MINTvp, and pulsation temperature ΔTvp of temperature Tvp(t) within one power cycle (Step S314).

Next, deterioration degree calculating unit 91 calculates deterioration degree Rvp of switching element Qvp in one power cycle in accordance with the expressions (D8) and (D14) (Step S315).

Next, deterioration amount calculating unit 92 calculates deterioration amount Svp of switching element Qvp in accordance with the expression (D20) (Step S316).

Next, deterioration ratio calculating unit 93 calculates deterioration ratio Svps of switching element Qvp in accordance with the expression (D26) (Step S317).

When one power cycle of temperature Twp(t) is terminated (YES in Step S318), deterioration degree calculating unit 91 derives maximum temperature MAXTwp, minimum temperature MINTwp, and pulsation temperature ΔTwp of temperature Twp(t) within one power cycle (Step S319).

Next, deterioration degree calculating unit 91 calculates deterioration degree Rwp of switching element Qwp in one power cycle in accordance with the expressions (D9) and (D15) (Step S320).

Next, deterioration amount calculating unit 92 calculates deterioration amount Swp of switching element Qwp in accordance with the expression (D21) (Step S321).

Next, deterioration ratio calculating unit 93 calculates deterioration ratio Swps of switching element Qwp in accordance with the expression (D27) (Step S322).

When one power cycle of temperature Tun(t) is terminated (YES in Step S323), deterioration degree calculating unit 91 derives maximum temperature MAXTun, minimum temperature MINTun, and pulsation temperature ΔTun of temperature Tun(t) within one power cycle (Step S324).

Next, deterioration degree calculating unit 91 calculates deterioration degree Run of switching element Qun in one power cycle in accordance with the expressions (D10) and (D16) (Step S325).

Next, deterioration amount calculating unit 92 calculates deterioration amount Sun of switching element Qun in accordance with the expression (D22) (Step S326).

Next, deterioration ratio calculating unit 93 calculates deterioration ratio Suns of switching element Qun in accordance with the expression (D28) (Step S327).

When one power cycle of temperature Tvn(t) is terminated (YES in Step S328), deterioration degree calculating unit 91 derives maximum temperature MAXTvn, minimum temperature MINTvn, and pulsation temperature ΔTvn of temperature Tvn(t) within one power cycle (Step S329).

Next, deterioration degree calculating unit 91 calculates deterioration degree Rvn of switching element Qvn in one power cycle in accordance with the expressions (D11) and (D17) (Step S330).

Next, deterioration amount calculating unit 92 calculates deterioration amount Svn of switching element Qvn in accordance with the expression (D23) (Step S331).

Next, deterioration ratio calculating unit 93 calculates deterioration ratio Svns of switching element Qvn in accordance with expression (D29) (Step S332).

When one power cycle of temperature Twn(t) is terminated (YES in Step S333), deterioration degree calculating unit 91 derives maximum temperature MAXTwn, minimum temperature MINTwn, and pulsation temperature ΔTwn of temperature Twn(t) within one power cycle (Step S334).

Next, deterioration degree calculating unit 91 calculates deterioration degree Rwn of switching element Qwn in one power cycle in accordance with the expressions (D12) and (D18) (Step S335).

Next, deterioration amount calculating unit 92 calculates deterioration amount Swn of switching element Qwn in accordance with the expression (D24) (Step S336).

Next, deterioration ratio calculating unit 93 calculates deterioration ratio Swns of switching element Qwn in accordance with the expression (D30) (Step S337).

When the power supply is in the on-state (NO in Step S338), the processing from Step S301 is repeated. Moreover, when the power supply turned off (YES in Step S338), the processing is terminated.

Referring back to FIG. 19, external control unit 500 transmits 3-bit select signal SL through select terminal PDS.

Output unit 5 outputs a deterioration ratio corresponding to select signal SL per power cycle in accordance with the relationship shown in FIG. 22. When select signal SL is "000," output unit 5 generates a signal setting a maximum value among deterioration ratio Sups, deterioration ratio Svps, deterioration ratio Swps, deterioration ratio Suns, deterioration ratio Svns, and deterioration ratio Swns (in other words, a ratio of a consumed service life with respect to an expected service life of a switching element having a shortest remaining service life) to be an on-pulse or off-pulse duty ratio, and outputs the same from output terminal PD.

When select signal SL is "001," output unit 5 generates a signal setting deterioration ratio Sups of switching element Qup to be an on-pulse or off-pulse duty ratio, and outputs the same from output terminal PD.

When select signal SL is "010," output unit 5 generates a signal setting deterioration ratio Svps of switching element Qvp to be an on-pulse or off-pulse duty ratio, and outputs the same from output terminal PD.

When select signal SL is "011," output unit 5 generates a signal setting deterioration ratio Swps of switching element Qwp to be an on-pulse or off-pulse duty ratio, and outputs the same from output terminal PD.

When select signal SL is "100," output unit 5 generates a signal setting deterioration ratio Suns of switching element Qun to be an on-pulse or off-pulse duty ratio, and outputs the same from output terminal PD.

When select signal SL is "101," output unit 5 generates a signal setting deterioration ratio Svns of switching element Qvn to be an on-pulse or off-pulse duty ratio, and outputs the same from output terminal PD.

When select signal SL is "110," output unit 5 generates a signal setting deterioration ratio Swns of switching element Qwn to be an on-pulse or off-pulse duty ratio, and outputs the same from output terminal PD.

When select signal SL is "111," output unit 5 generates a signal setting a minimum value among deterioration ratio Sups, deterioration ratio Svps, deterioration ratio Swps, deterioration ratio Suns, deterioration ratio Svns, and deterioration ratio Swns to be an on-pulse or off-pulse duty ratio, and outputs the same from output terminal PD.

As described above, according to the present embodiment, similarly to the first embodiment, the number of A/D converters and insulating elements can be reduced, so that the service life diagnosis can be performed with a small circuit configuration. Consequently, increase in size of the power module can be prevented. Moreover, since temperature information of a switching element (semiconductor chip) which has not been detected is estimated, an accurate service life diagnosis can be performed even in the case where temperatures of elements are imbalanced such as during the motor locking.

Modified Example 1 of Third Embodiment

In the present modified example, output unit 5 generates a serial signal including a start bit, deterioration ratio (b0 to b5), and stop bits per power cycle as shown in FIG. 7, and outputs the same from output terminal PD.

When select signal SL is "000," output unit 5 generates a serial signal including a start bit, a maximum value among deterioration ratio Sups, deterioration ratio Svps, deterioration ratio Swps, deterioration ratio Suns, deterioration ratio Svns, and deterioration ratio Swns (6-bits) (in other words, a ratio of a consumed service life with respect to an expected service life of a switching element having a shortest remaining service life), and stop bits, and outputs the same from output terminal PD.

When select signal SL is "001," output unit 5 generates a serial signal including a start bit, 6-bit deterioration ratio Sups, and stop bits, and outputs the same from output terminal PD. When select signal SL is "010," output unit 5 generates a serial signal including a start bit, 6-bit deterioration ratio Svps, and stop bits, and outputs the same from output terminal PD.

When select signal SL is "011," output unit 5 generates a serial signal including a start bit, 6-bit deterioration ratio Swps, and stop bits, and outputs the same from output terminal PD. When select signal SL is "100," output unit 5 generates a serial signal including a start bit, 6-bit deterioration ratio Suns, and stop bits, and outputs the same from output terminal PD.

When select signal SL is "101," output unit 5 generates a serial signal including a start bit, 6-bit deterioration ratio Svns, and stop bits, and outputs the same from output terminal PD. When select signal SL is "110," output unit 5 generates a serial signal including a start bit, 6-bit deterioration ratio Swns, and stop bits, and outputs the same from output terminal PD.

When select signal SL is "111," output unit 5 generates a serial signal including a start bit, a minimum value among deterioration ratio Sups, deterioration ratio Svps, deterioration ratio Swps, deterioration ratio Suns, deterioration ratio Svns, and deterioration ratio Swns (6-bits) (in other words, a ratio of a consumed service life with respect to an expected service life of a switching element having a longest remaining service life), and stop bits, and outputs the same from output terminal PD.

It should be noted that, although the deterioration ratio is expressed by 6-bits in the modified example described above, this is one example, and the deterioration ratio may be expressed by n-bits (n is a natural number greater than or equal to 1).

Modified Example 2 of Third Embodiment

Figure 23:
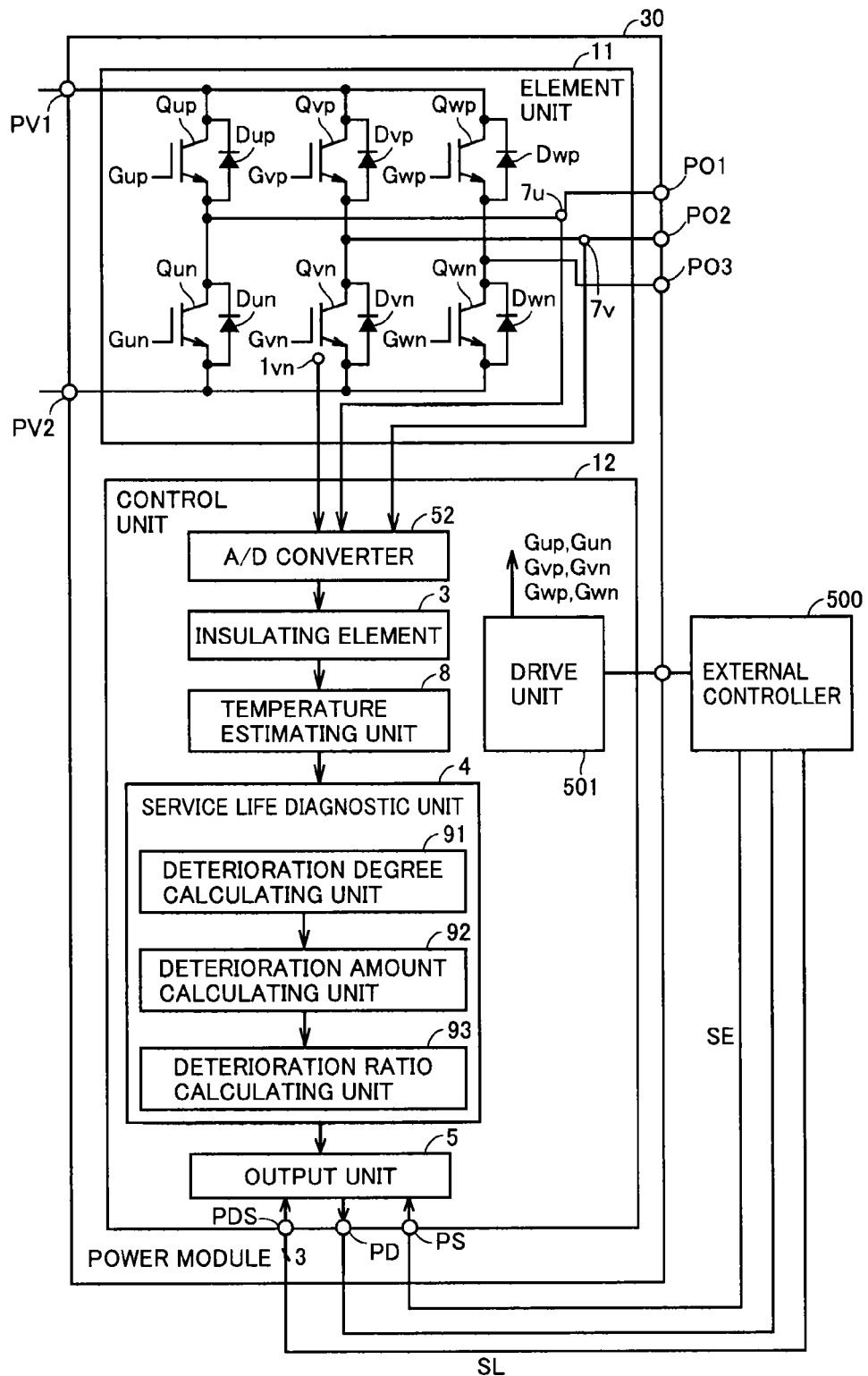
FIG. 23 represents a configuration of a power module of a modified example 2 of the third embodiment.

FIG. 23 represents a configuration of a power module of a modified example 2 of the third embodiment.

This power module 30 further includes a select terminal PS in addition to select terminal PDS which is similar to that of the third embodiment and modified example 1 of the third embodiment.

External control unit 500 transmits 1-bit select signal SE through select terminal PS. Select signal SE is a signal which designates if output unit 5 outputs a diagnostic result in an analog method described in the third embodiment or outputs a diagnostic result in a digital method described in modified example 1 of the third embodiment.

When select signal SE is "1," and select signal SL is "000," output unit 5 generates a signal setting a maximum value among deterioration ratio Sups, deterioration ratio Svps, deterioration ratio Swps, deterioration ratio Suns, deterioration ratio Svns, and deterioration ratio Swns (in other words, a ratio of a consumed service life with respect to an expected service life of a switching element having a shortest remaining service life) to be an on-pulse or off-pulse duty ratio, and outputs the same from output terminal PD.

When select signal SE is "1," and select signal SL is "001," output unit 5 generates a signal setting deterioration ratio Sups of switching element Qup to be an on-pulse or off-pulse duty ratio, and outputs the same from output terminal PD.

When select signal SE is "1," and select signal SL is "010," output unit 5 generates a signal setting deterioration ratio Svps of switching element Qvp to be an on-pulse or off-pulse duty ratio, and outputs the same from output terminal PD.

When select signal SE is "1," and select signal SL is "011," output unit 5 generates a signal setting deterioration ratio Swps of switching element Qwp to be an on-pulse or off-pulse duty ratio, and outputs the same from output terminal PD.

When select signal SE is "1," and select signal SL is "100," output unit 5 generates a signal setting deterioration ratio Suns of switching element Qun to be an on-pulse or off-pulse duty ratio, and outputs the same from output terminal PD.

When select signal SE is "1," and select signal SL is "101," output unit 5 generates a signal setting deterioration ratio Svns of switching element Qvn to be an on-pulse or off-pulse duty ratio, and outputs the same from output terminal PD.

When select signal SE is "1," and select signal SL is "110," output unit 5 generates a signal setting deterioration ratio Swns of switching element Qwn to be an on-pulse or off-pulse duty ratio, and outputs the same from output terminal PD.

When select signal SE is "1," and select signal SL is "111," output unit 5 generates a signal setting a minimum value among deterioration ratio Sups, deterioration ratio Svps, deterioration ratio Swps, deterioration ratio Suns, deterioration ratio Svns, and deterioration ratio Swns (in other words, a ratio of a consumed service life with respect to an expected service life of a switching element having a shortest remaining service life) to be an on-pulse or off-pulse duty ratio, and outputs the same from output terminal PD.

When select signal SE is "0," and select signal SL is "000," output unit 5 generates a serial signal including a start bit, a maximum value among deterioration ratio Sups, deterioration ratio Svps, deterioration ratio Swps, deterioration ratio Suns, deterioration ratio Svns, and deterioration ratio Swns (6-bits) (in other words, a ratio of a consumed service life with respect to an expected service life of a switching element having a shortest remaining service life), and stop bits, and outputs the same from output terminal PD.

When select signal SE is "0," and select signal SL is "001," output unit 5 generates a serial signal including a start bit, 6-bit deterioration ratio Sups, stop bits, and outputs the same from output terminal PD.

When select signal SE is "0," and select signal SL is "010," output unit 5 generates a serial signal including a start bit, 6-bit deterioration ratio Svps, and stop bits, and outputs the same from output terminal PD.

When select signal SE is "0," and select signal SL is "011," output unit 5 generates a serial signal including a start bit, 6-bit deterioration ratio Swps, and stop bits, and outputs the same from output terminal PD.

When select signal SE is "0," and select signal SL is "100," output unit 5 generates a serial signal including a start bit, 6-bit deterioration ratio Suns, and stop bits, and outputs the same from output terminal PD.

When select signal SE is "0," and select signal SL is "101," output unit 5 generates a serial signal including a start bit, 6-bit deterioration ratio Svns, and stop bits, and outputs the same from output terminal PD.

When select signal SE is "0," and select signal SL is "110," output unit 5 generates a serial signal including a start bit, 6-bit deterioration ratio Swns, and stop bits, and outputs the same from output terminal PD.

When select signal SE is "0," and select signal SL is "111," output unit 5 generates a serial signal including a start bit, a minimum value among deterioration ratio Sups, deterioration ratio Svps, deterioration ratio Swps, deterioration ratio Suns, deterioration ratio Svns, and deterioration ratio Swns (6-bits) (in other words, a ratio of a consumed service life with respect to an expected service life of a switching element having a shortest remaining service life), and stop bits, and outputs the same from output terminal PD.

It should be noted that, although the deterioration ratio is expressed by 6-bits in the modified example described above, this is one example, and the deterioration ratio may be expressed by n-bits (n is a natural number greater than or equal to 1).

Modified Example 3 of Third Embodiment

Figure 24:
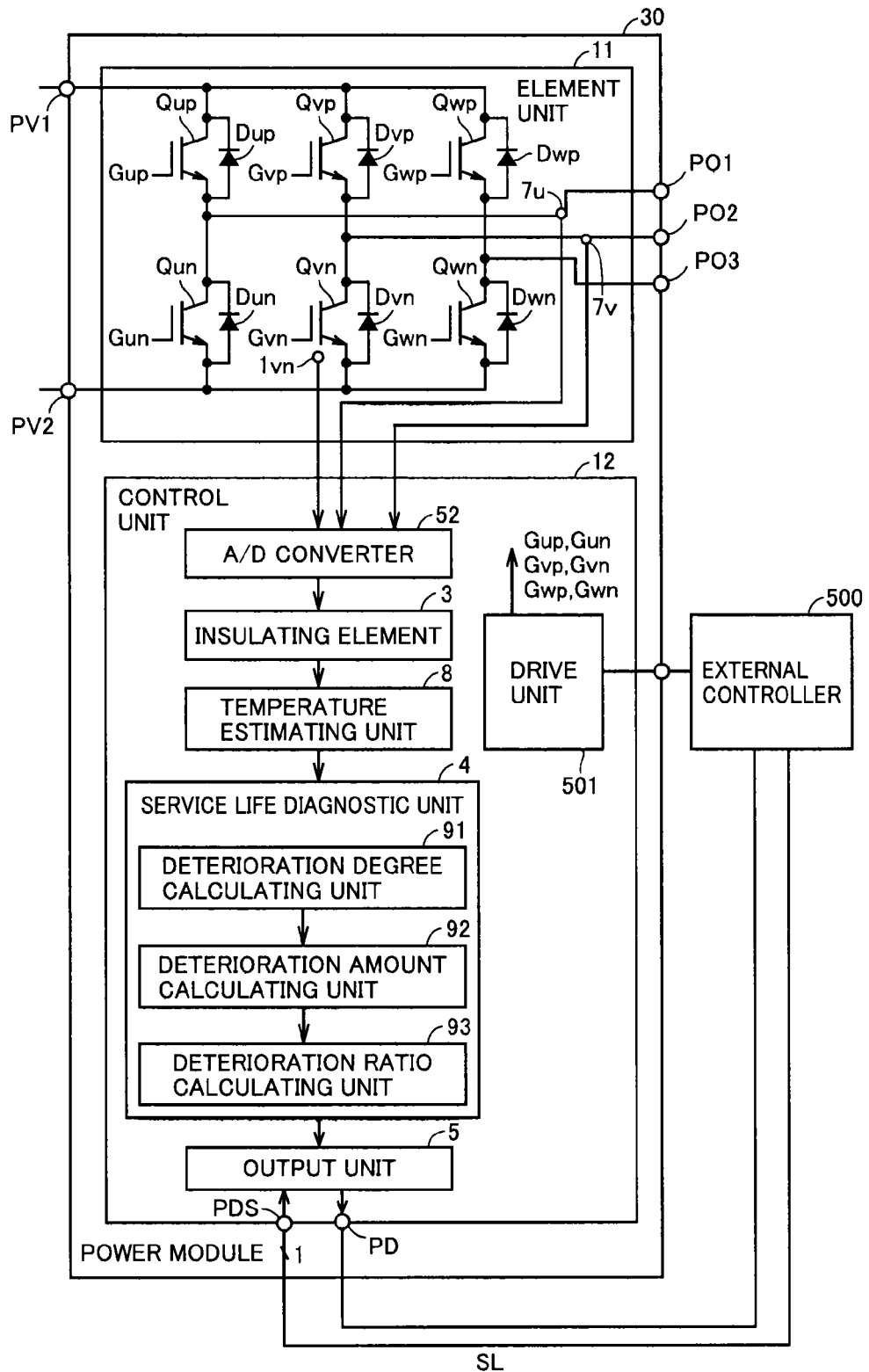
FIG. 24 represents a configuration of a power module of a modified example 3 of the third embodiment.

FIG. 24 represents a configuration of a power module of a modified example 3 of the third embodiment.

Figure 25:
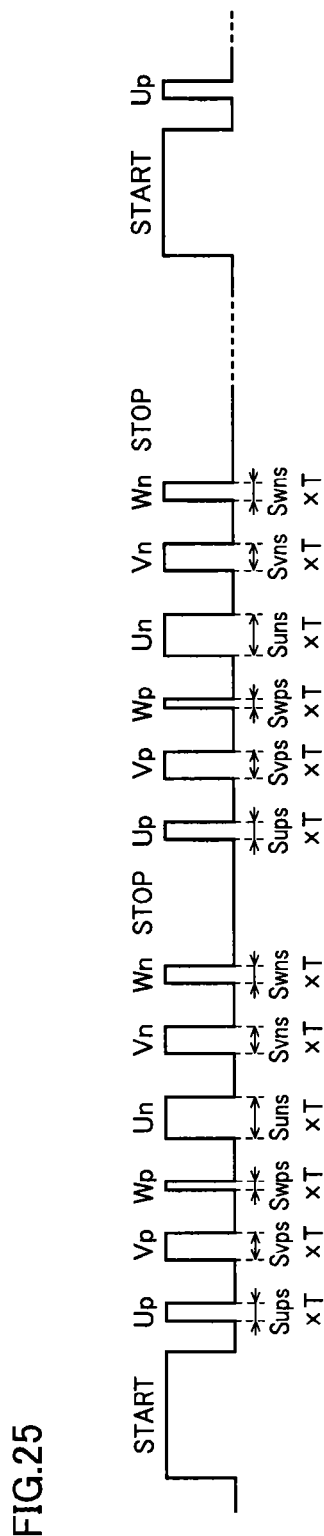
FIG. 25 represents an example of a signal outputted from an output terminal PD in the case where a select signal SL is "1" in a modified example 3 of the third embodiment.

FIG. 25 represents an example of a signal outputted from output terminal PD when select signal SL is "1" in modified example 3 of the third embodiment.

External control unit 500 transmits 1-bit select signal SL through select terminal PDS.

When select signal SL is "0," output unit 5 generates a signal setting a maximum value among deterioration ratio Sups, deterioration ratio Svps, deterioration ratio Swps, deterioration ratio Suns, deterioration ratio Svns, and deterioration ratio Swns (in other words, a ratio of a consumed service life with respect to an expected service life of a switching element having a shortest remaining service life) to be an on-pulse or off-pulse duty ratio, and outputs the same from output terminal PD.

When select signal SL is "1," output unit 5, as shown in FIG. 25, includes START (the "H" level continues) and STOP (the "L" level continues), generates a signal setting deterioration ratio Sups, deterioration ratio Svps, deterioration ratio Swps, deterioration ratio Suns, deterioration ratio Svns, and deterioration ratio Swns to be first to sixth on-pulse or off-pulse duty ratios, and outputs the same from output terminal PD.

Modified Example 4 of Third Embodiment

Figure 26:
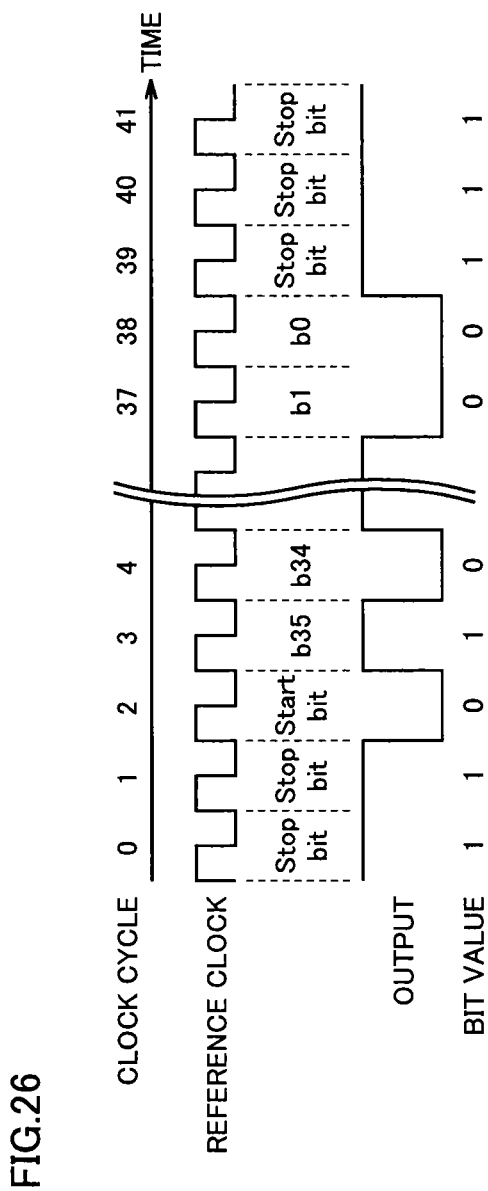
FIG. 26 represents an example of a signal outputted from an output terminal PD in the case where a select signal SL is "1" in a modified example 4 of the third embodiment.

FIG. 26 represents an example of a signal outputted from output terminal PD when select signal SL is "1" in a modified example 4 of the third embodiment.

In the present modified example, when select signal SL is "0," output unit 5 generates a serial signal including a start bit, a maximum value among deterioration ratio Sups, deterioration ratio Svps, deterioration ratio Swps, deterioration ratio Suns, deterioration ratio Svns, and deterioration ratio Swns (6-bits) (in other words, a ratio of a consumed service life with respect to an expected service life of a switching element having a shortest remaining service life), and stop bits as shown in FIG. 7, and outputs the same from output terminal PD.

When select signal SL is "1," output unit 5 generates a serial signal including a start bit, deterioration ratio Sups (b30 to b35), deterioration ratio Svps (b24 to b29), deterioration ratio Swps (b18 to b23), deterioration ratio Suns (b12 to b17), deterioration ratio Svns (b6 to b11), deterioration ratio Swns (b0 to b5), and stop bits, and outputs the same from output terminal PD.

It should be noted that, although the deterioration ratio is expressed by 6-bits in the modified example described above, this is one example, and the deterioration ratio may be expressed by n-bits (n is a natural number greater than or equal to 1).

Modified Example 5 of Third Embodiment

Figure 27:
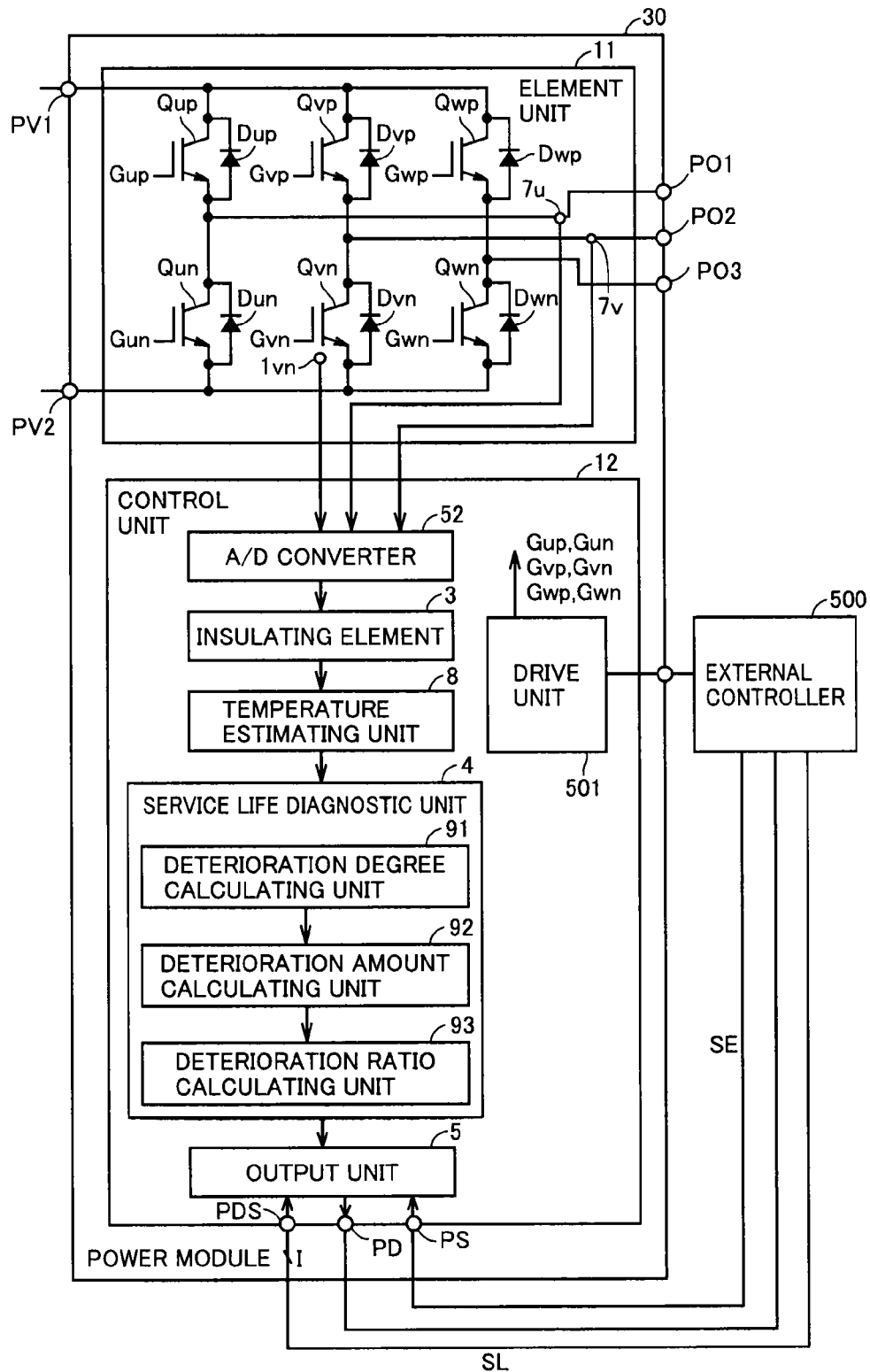
FIG. 27 represents a configuration of a power module of a modified example 5 of the third embodiment.

FIG. 27 represents a configuration of a power module of a modified example 5 of the third embodiment.

This power module 10 further includes select terminal PS in addition to select terminal PDS which is similar to that of modified example 3 of the third embodiment and modified example 4 of the third embodiment.

External control unit 500 transmits 1-bit select signal SE through select terminal PS. Select signal SE is a signal which designates if output unit 5 outputs a diagnostic result in an analog method described in modified example 3 of the third embodiment or outputs a diagnostic result in a digital method described in modified example 4 of the third embodiment.

When select signal SE is "1," and select signal SL is "0," output unit 5 generates a signal setting a maximum value among deterioration ratio Sups, deterioration ratio Svps, deterioration ratio Swps, deterioration ratio Suns, deterioration ratio Svns, and deterioration ratio Swns (in other words, a ratio of a consumed service life with respect to an expected service life of a switching element having a shortest remaining service life) to be an on-pulse or off-pulse duty ratio, and outputs the same from output terminal PD.

When select signal SE is "1," and select signal SL is "1," output unit 5 includes START (the "H" level continues) and STOP (the "L" level continues), generates a signal setting deterioration ratio Sups, deterioration ratio Svps, deterioration ratio Swps, deterioration ratio Suns, deterioration ratio Svns, and deterioration ratio Swns to be first to sixth on-pulse or off-pulse duty ratios, and outputs the same from output terminal PD.

When select signal SE is "0," and select signal SL is "0," output unit 5 generates a serial signal including a start bit, a maximum value among deterioration ratio Sups, deterioration ratio Svps, deterioration ratio Swps, deterioration ratio Suns, deterioration ratio Svns, and deterioration ratio Swns (6-bits) (in other words, a ratio of a consumed service life with respect to an expected service life of a switching element having a shortest remaining service life), and stop bits, and outputs the same from output terminal PD.

When select signal SE is "0," and select signal SL is "1," output unit 5 generates a serial signal including a start bit, deterioration ratio Sups (b30 to b35), deterioration ratio Svps (b24 to b29), deterioration ratio Swps (b18 to b23), deterioration ratio Suns (b12 to b17), deterioration ratio Svns (b6 to b11), deterioration ratio Swns (b0 to b5), and stop bits, and outputs the same from output terminal PD.

It should be noted that, although the deterioration ratio is expressed by 6-bits in the modified example described above, this is one example, and the deterioration ratio may be expressed by n-bits (n is a natural number greater than or equal to 1).

Modified Example 6 of Third Embodiment

Figure 28:
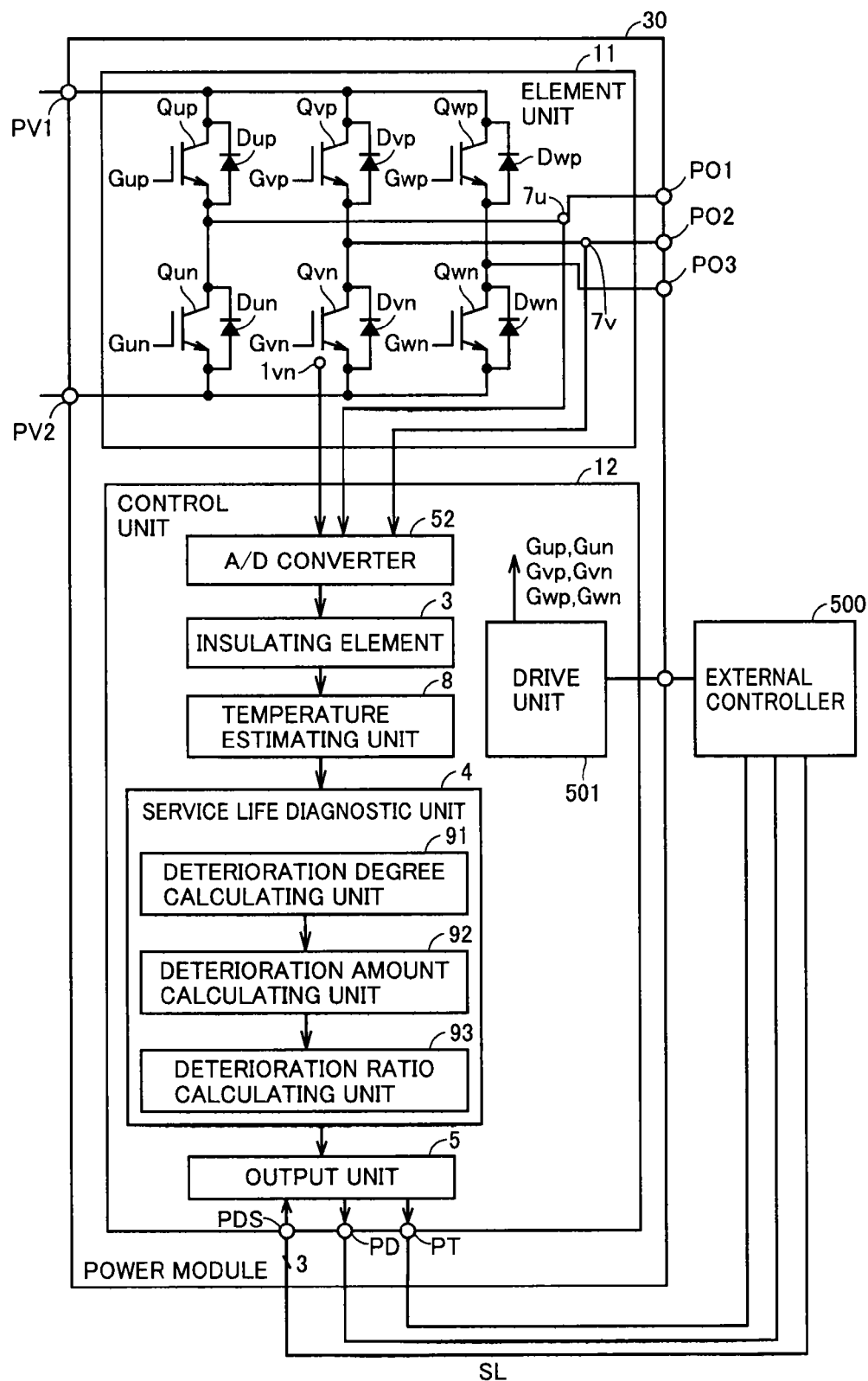
FIG. 28 represents a configuration of a power module of a modified example 6 of the third embodiment.

FIG. 28 represents a configuration of a power module of a modified example 6 of the third embodiment.

This power module 30 includes output terminal PT.

Output unit 5 generates a serial signal including a start bit, 6-bit maximum temperature MAXTup, 6-bit minimum temperature MINTup, 6-bit pulsation temperature ΔTup, 6-bit maximum temperature MAXTvp, 6-bit minimum temperature MINTvp, 6-bit pulsation temperature ΔTvp, 6-bit maximum temperature MAXTwp, G-bit minimum temperature MINTwp, 6-bit pulsation temperature ΔTwp, 6-bit maximum temperature MAXTun, 6-bit minimum temperature MINTun, 6-bit pulsation temperature ΔTun, 6-bit maximum temperature MAXTvn, 6-bit minimum temperature MINTvn, 6-bit pulsation temperature ΔTvn, 6-bit maximum temperature MAXTwn, G-bit minimum temperature MINTwn, 6-bit pulsation temperature ΔTwn, and stop bits per power cycle, and outputs the same from output terminal PT.

It should be noted that output unit 5 may output some temperatures among the eighteen temperatures described above from output terminal PT.

Moreover, output unit 5 may output an average of maximum temperature MAXTup and minimum temperature MINTup, an average of maximum temperature MAXTvp and minimum temperature MINTvp, an average of maximum temperature MAXTwp and minimum temperature MINTwp, an average of maximum temperature MAXTun and minimum temperature MINTun, an average of maximum temperature MAXTvn and minimum temperature MINTvn, and an average of maximum temperature MAXTwn and minimum temperature MINTwn per power cycle.

It should be noted that, although the deterioration ratio is expressed by 6-bits in the modified example described above, this is one example, and the deterioration ratio may be expressed by n-bits (n is a natural number greater than or equal to 1).

Fourth Embodiment

Figure 29:
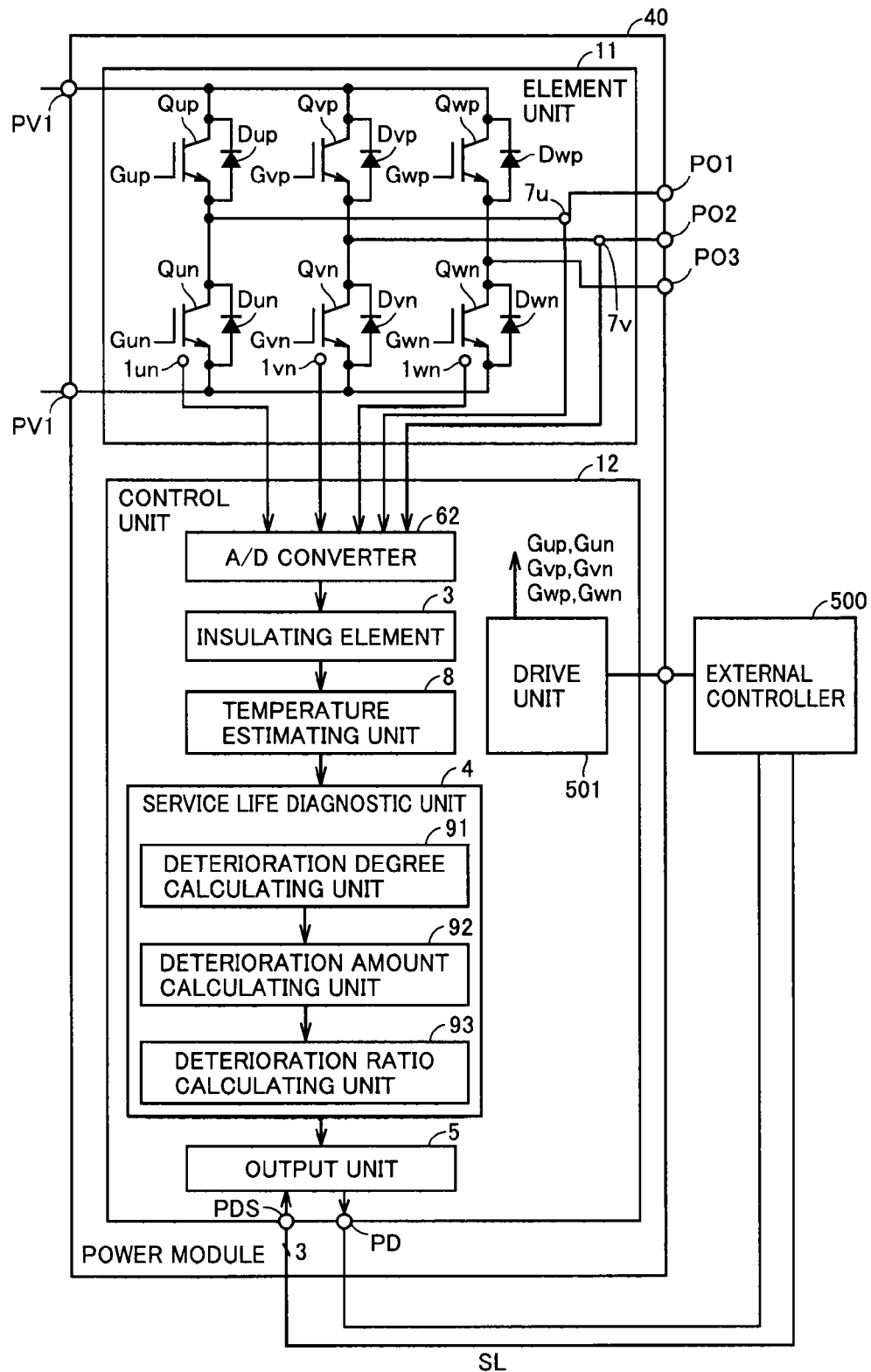
FIG. 29 represents a configuration of a power module of a fourth embodiment.

FIG. 29 represents a configuration of a power module of a fourth embodiment.

A power module 40 of FIG. 29 is different from power module 30 of FIG. 18 on the following points.

A/D converter 62 converts an analog signal representing a temperature transmitted from temperature sensor 1un into a digital signal Tun(t). A/D converter 2 converts an analog signal representing a temperature transmitted from temperature sensor 1vn into a digital signal Tvn(t). A/D converter 2 converts an analog signal representing a temperature transmitted from temperature sensor 1wn into a digital signal Twn(t).

A/D converter 62 convents an analog signal representing a U-phase current transmitted from current sensor 7u into a digital signal. A/D converter 2 converts an analog signal representing a V-phase current transmitted from current sensor 7v into a digital signal.

A/D converter 62 has five input channels and one output channel. By sequentially designating input channels subjected to the A/D conversion, signals from temperature sensors 1un, 1vn, 1wn and current sensors 7u, 7v are converted into digital signals.

Digital signals Tun(t), Tvn(t), Twn(t) representing temperatures, digital signal Iu(t) representing a U-phase current, and digital signal Iv(t) representing a V-phase current outputted from A/D converter 62 are transmitted to temperature estimating unit 8 through insulating element 3.

Temperature estimating unit 8, similarly to the third embodiment, derives a W-phase current Iw(t) from U-phase current Iu(t) and V-phase current Iv(t) in accordance with the Kirchhoff expression (C1).

Temperature estimating unit 8, similarly to the third embodiment, calculates a current Iup(t) flowing to switching element Qup, a current Ivp(t) flowing to switching element Qvp, a current Iwp(t) flowing to switching element Qwp, a current Iun(t) flowing to switching element Qun, a current Ivn(t) flowing to switching element Qvn, and a current Iwn(t) flowing to switching element Qwn in accordance with the expressions (C2) to (C7).

Temperature estimating unit 8 calculates calorific value Hup of switching element Qup, calorific value Hvp of switching element Qvp, calorific value Hwp of switching element Qwp, calorific value Hun of switching element Qun, calorific value Hvn of switching element Qvn, and calorific value Hwn of switching element Qwn per temperature calculation cycle Δt in accordance with the expressions (C8) to (C25).

Temperature estimating unit 8 calculates base temperatures Tbun, Tbvn, Tbwn per temperature calculation cycle Δt in accordance with the expressions (E1) to (E3).

[Expression 19]

$$Tbun = Tun - Rth\frac{1}{\Delta t}\int_{t1}^{t2} Hun\, dt \quad (E1)$$

$$Tbvn = Tvn - Rth\frac{1}{\Delta t}\int_{t1}^{t2} Hvn\, dt \quad (E2)$$

$$Tbwn = Twn + Rth\frac{1}{\Delta t}\int_{t1}^{t2} Hwn\, dt \quad (E3)$$

Herein, the item Rth is a thermal resistance between a chip and a case.

Temperature estimating unit 8 calculates an average Tb of base temperatures Tbun, Tbvn, Tvwn in accordance with the expression (E4).

$$Tb=(Tbun+Tbvn+Tbwn)/3 \qquad (E4)$$

(Operation of Service Life Diagnosis)

Figure 30:
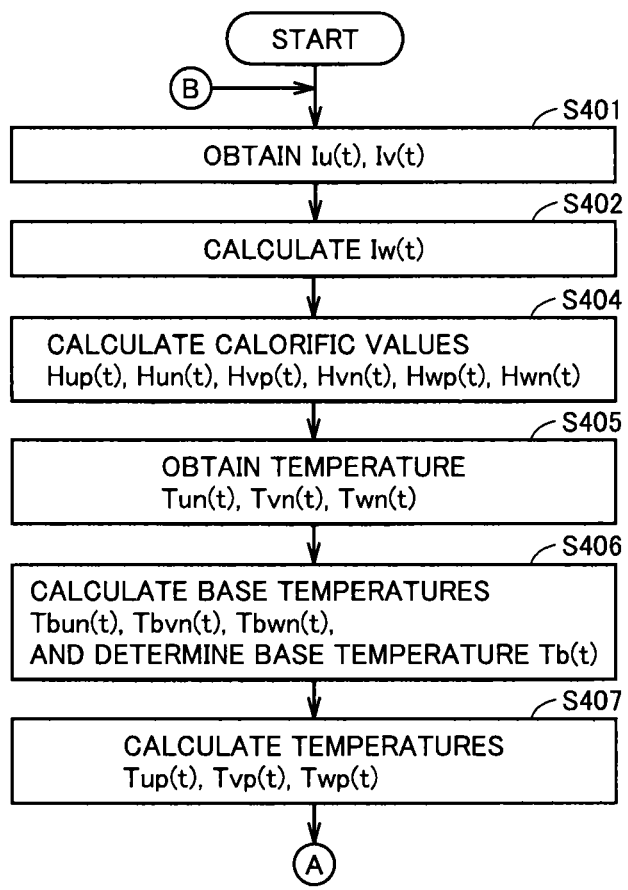
FIG. 30 is a flowchart representing operation procedures for a service life diagnosis of the fourth embodiment.
Figure 31:
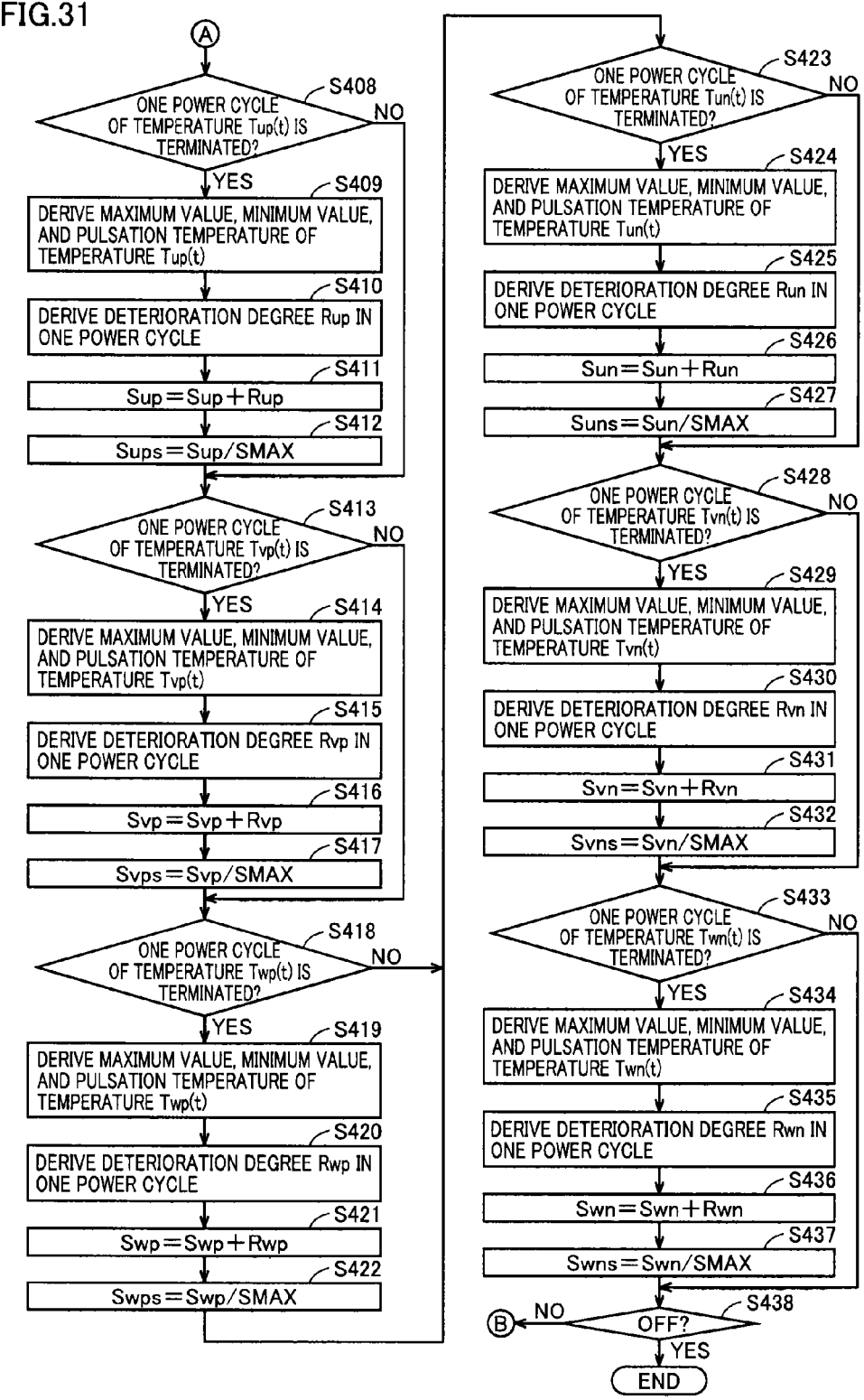
FIG. 31 is a flowchart representing operation procedures for a service life diagnosis of the fourth embodiment.

FIGS. 30 and 31 are flowcharts representing operation procedures for the service life diagnosis of the fourth embodiment.

Referring to FIGS. 30 and 31, temperature estimating unit 8 obtains U-phase current Iu(t) and V-phase current Iv(t) (Step S401).

Next, temperature estimating unit 8 derives W-phase current Iw(t) in accordance with the expression (C1) (Step S402).

Next, temperature estimating unit 8 calculates calorific value Hup of switching element Qup, a calorific value Hvp of switching element Qvp, calorific value Hwp of switching element Qwp, calorific value Hun of switching element Qun, calorific value Hvn of switching element Qvn, and calorific value Hwn of switching element Qwn per temperature calculation cycle Δt in accordance with the expressions (C2) to (C31) (Step S404).

Next, temperature estimating unit 8 obtains temperatures Tun(t), Tvn(t), Twn(t) per temperature calculation cycle Δt (Step S405).

Next, temperature estimating unit 8 calculates base temperature Tb per temperature calculation cycle Δt in accordance with the expressions (E1) to (E4) (Step S406).

Next, temperature estimating unit 8 calculates temperatures Tup(t), Tvp(t), Twp(t) per temperature calculation cycle Δt in accordance with the expressions (C33) to (C35) (Step S407).

When one power cycle of temperature Tup(t) is terminated (YES in Step S408), deterioration degree calculating unit 91 derives maximum temperature MAXTup, minimum temperature MINTup, and pulsation temperature ΔTup of temperature Tup(t) within one power cycle (Step S409).

Next, deterioration degree calculating unit 91 calculates deterioration degree Rup of switching element Qup in one power cycle in accordance with the expressions (D7) and (D13) (Step S410).

Next, deterioration amount calculating unit 92 calculates deterioration amount Sup of switching element Qup in accordance with the expression (D19) (Step S411).

Next, deterioration ratio calculating unit 93 calculates deterioration ratio Sups of switching element Qup in accordance with the expression (D25) (Step S412).

When one power cycle of temperature Tvp(t) is terminated (YES in Step S413), deterioration degree calculating unit 91 derives maximum temperature MAXTvp, minimum temperature MINTvp, and pulsation temperature ΔTvp of temperature Tvp(t) within one power cycle (Step S414).

Next, deterioration degree calculating unit 91 calculates deterioration degree Rvp of switching element Qvp in one power cycle in accordance with the expression (D8) and (D14) (Step S415).

Next, deterioration amount calculating unit 92 calculates deterioration amount Svp of switching element Qvp in accordance with the expression (D20) (Step S416).

Next, deterioration ratio calculating unit 93 calculates deterioration ratio Svps of switching element Qvp in accordance with the expression (D26) (Step S417).

When one power cycle of temperature Twp(t) is terminated (YES in Step S418), deterioration degree calculating unit 91 derives maximum temperature MAXTwp, minimum temperature MINTwp, and pulsation temperature ΔTwp of temperature twp(t) within one power cycle (Step S419).

Next, deterioration degree calculating unit 91 calculates deterioration degree Rwp of switching element Qwp in one power cycle in accordance with the expressions (D9) and (D15) (Step S420).

Next, deterioration amount calculating unit 92 calculates deterioration amount Swp of switching element Qwp in accordance with the expression (D21) (Step S421).

Next, deterioration ratio calculating unit 93 calculates deterioration ratio Swps of switching element Qwp in accordance with the expression (D27) (Step S422).

When one power cycle of temperature Tun(t) is terminated (YES in Step S423), deterioration degree calculating unit 91 derives maximum temperature MAXTun, minimum temperature MINTun, and pulsation temperature ΔTun of temperature Tun(t) within one power cycle (Step S424).

Next, deterioration degree calculating unit 91 calculates deterioration degree Run of switching element Qun in one power cycle in accordance with the expressions (D10) and (D16) (Step S425).

Next, deterioration amount calculating unit 92 calculates deterioration amount Sun of switching element Qun in accordance with the expression (D22) (Step S426).

Next, deterioration ratio calculating unit 93 calculates deterioration ratio Suns of switching element Qun in accordance with the expression (D28) (Step S427).

When one power cycle of temperature Tvn(t) is terminated (YES in S428), deterioration degree calculating unit 91 derives maximum temperature MAXTvn, minimum temperature MINTvn, and pulsation temperature ΔTvn of temperature Tvn(t) within one power cycle (Step S429).

Next, deterioration degree calculating unit 91 calculates deterioration degree Rvn of switching element Qvn in one power cycle in accordance with the expressions (D11) and (D17) (Step S430).

Next, deterioration amount calculating unit 92 calculates deterioration amount Svn of switching element Qvn in accordance with the expression (D23) (Step S431).

Next, deterioration ratio calculating unit 93 calculates deterioration ratio Svns of switching element Qvn in accordance with the expression (D29) (Step S432).

When one power cycle of temperature Twn(t) is terminated (YES in Step S333), deterioration degree calculating unit 91 derives maximum temperature MAXTwn, minimum temperature MINTwn, and pulsation temperature ΔTwn of temperature Twn(t) within one power cycle (Step S434).

Next, deterioration degree calculating unit 91 calculates deterioration degree Rwn of switching element Qwn in one power cycle in accordance with the expressions (D12) and (D18) (Step S435).

Next, deterioration amount calculating unit 92 calculates deterioration amount Swn of switching element Qwn in accordance with the expression (D24) (Step S436).

Next, deterioration ratio calculating unit 93 calculates deterioration ratio Swns of switching element Qwn in accordance with the expression (D30) (Step S437).

When the power supply is in the on-state (NO in Step S438), the processing from Step S401 is repeated. Moreover, when the power supply is turned off (YES in Step S438), the processing is terminated.

As described above, according to the present embodiment, similarly to the first embodiment, the number of A/D converters and insulating elements can be reduced, so that the service life diagnosis can be performed with a small circuit configuration. Consequently, increase in size of the power module can be prevented. Moreover, by actually detecting temperatures of three elements in the lower arms, the service life diagnosis with a higher accuracy can be performed, and a temperature of a semiconductor chip which is not detected is estimated. Therefore, an accurate service life diagnosis can be performed even in the case where temperatures of elements are imbalanced such as during the motor locking.

Fifth Embodiment

In the embodiments described above, deterioration degree calculating unit 91 calculates a deterioration degree regardless of a magnitude of a pulsation temperature.

On the other hand, according to the present embodiment, deterioration degree calculating unit 91 calculates a deterioration degree only when a magnitude of the pulsation temperature exceeds a threshold value (for example, 10° C.).

Sixth Embodiment

In the embodiments described above, deterioration ratio calculating unit 93 divides a deterioration amount of a switching element by deterioration amount SMAX provided after having reached an expected service life to calculate deterioration ratio Svns of switching element Qvn. The deterioration degree calculated in such a manner represented a ratio of a consumed service life with respect to an expected service life of a switching element.

In the present embodiment, as shown in the expressions (F1) to (F6), deterioration ratio calculating unit 93 calculates a value which is obtained by dividing a deterioration amount of a switching element by deterioration amount SMAX provided after having reached an expected service life to obtain a deterioration ratio and subtracting the deterioration ratio from 1. The items Sups', Svps', Swps', Suns', Svns', Swns' obtained in such a manner represents a ratio of a remaining service life with respect to an expected service life of a switching element.

$$Sups'=1-Sup/S\,MAX \quad (F1)$$

$$Svps'=1-Svp/S\,MAX \quad (F2)$$

$$Swps'=1-Swp/S\,MAX \quad (F3)$$

$$Suns'=1-Sun/S\,MAX \quad (F4)$$

$$Svns'=1-Svn/S\,MAX \quad (F5)$$

$$Swns'=1-Swn/S\,MAX \quad (F6)$$

In the embodiments described above, output unit 5 outputs Sups, Svps, Swps, Suns, Svns, Swns. Instead, output unit 5 may output Sups', Svps', Swps', Suns', Svns', Swns'.

In the second embodiment, when select signal SL is "00," output unit 5 can output a minimum value among Suns', Svns', and Swns' (in other words, a ratio of a remaining service life with respect to an expected service life of a switching element having a shorter remaining service life).

Moreover, in the third embodiment, when select signal SL is "000," output unit 5 can output a minimum value among Sups', Svps', Swps', Suns', Svns', and Swns' (in other words, a ratio of a consumed service life with respect to an expected service life of a switching element having a shortest remaining service life).

Moreover, when select signal SL is "111," output unit 5 can output a minimum value among Sups', Svps', Swps', Suns', Svns', Swns' (in other words, a ratio of a remaining service life with respect to an expected service life of a switching element having a longest remaining service life).

Seventh Embodiment

In the embodiments described above, deterioration ratio calculating unit 93 calculates deterioration ratios Sups, Svps, Swps, Suns, Svns, Swns regardless of magnitudes of deterioration amounts Sup, Svp, Swp, Sun, Svn, Swn.

On the other hand, according to the present embodiment, deterioration ratio calculating unit 93 calculates deterioration ratios Sups, Svps, Swps, Suns, Svns, Swns in accordance with the expressions (D25) to (D30) when deterioration amounts Sup, Svp, Swp, Sun, Svn, Swn exceed deterioration amount SMAX of an expected service life.

It should be understood that the embodiments disclosed herein are only by way of examples, and not to be taken by way of limitation. Therefore, the technical scope of the present invention is not limited by the description above, but rather by the terms of the appended claims. Further, any modifications within the scope and meaning equivalent to the terms of the claims are included.

REFERENCE SIGNS LIST $1un$, $1vn$, $1wn$ temperature sensor; 2, 52, 62 A/D converter; 3 insulating element; 4 service life diagnostic unit; 5 output unit; $7u$, $7v$ temperature sensor; 10, 20, 30, 40 power module; 11 element unit; 12 control unit; 91 deterioration degree calculating unit; 92 deterioration amount calculating unit; 93 deterioration degree calculating unit; 101, 102 solder; 105, 106 copper pattern; 110 insulating substrate; 112 base plate; 114 heat sink; 116 case; 500 external control unit; 501 drive unit; PD, PDS, PT, PO1, PO2, PO3 output terminal; PDS, PS select terminal; PV1, PV2 voltage terminal; Qup, Qvp, Qwp, Qun, Qvn, Qwn switching element; Dup, Dvp, Dwp, Dun, Dvn, Dwn diode element.

The invention claimed is:

1. A power module, comprising:
   a plurality of semiconductor chips;
   one or more temperature sensor provided in a periphery of at least one semiconductor chip of said plurality of semiconductor chips;
   one A/D converter which converts an output from said temperature sensor into a digital signal;
   a diagnostic unit which diagnoses a service life of said power module based on a signal indicating a temperature outputted from said A/D converter;
   an output unit which generates a signal representing a diagnostic result; and
   an output terminal which outputs a signal representing said diagnostic result to outside,
   said diagnostic unit calculating a deterioration degree of said semiconductor chip per power cycle from a service life characteristic in a power cycle of said semiconductor chip, and calculating a sum total of deterioration degrees of a plurality of power cycles as a deterioration amount,
   said diagnostic unit calculating a deterioration degree of said semiconductor chip based on a maximum temperature, a minimum temperature, and a difference between said maximum temperature and said minimum temperature in one power cycle detected by said temperature sensor,
   said output unit outputting the signal representing said diagnostic result to an outside controller through the output terminal, and said outside controller controlling said plurality of semiconductor chips based on said diagnostic result.

2. The power module according to claim 1, wherein said diagnostic unit calculates a deterioration degree of said semiconductor chip based on an Arrhenius form expression including said maximum temperature, said minimum temperature, and a difference between said maximum temperature and said minimum temperature as variables.

3. The power module according to claim 1, wherein said diagnostic unit calculates a deterioration degree of said semiconductor chip only when a difference between said maximum temperature and said minimum temperature is greater than or equal to a threshold value.

4. The power module according to claim 1, wherein
said diagnostic unit calculates a ratio of a remaining service life with respect to an expected service life of said semiconductor chip based on said deterioration amount, and
said output unit outputs a signal representing said ratio from said output terminal to outside.

5. The power module according to claim 1, wherein
said diagnostic unit calculates a ratio of a consumed service life with respect to an expected service life of said semiconductor chip based on said deterioration amount, and
said output unit outputs a signal representing said ratio from said output terminal to outside.

6. The power module according to claim 1, wherein
when a deterioration amount of said semiconductor chip exceeds a deterioration amount corresponding to an expected service life, said diagnostic unit calculates a ratio of a consumed service life with respect to an expected service life of said semiconductor chip based on said deterioration amount, and
said output unit outputs a signal representing said ratio from said output terminal to outside.

7. The power module according to claim 1, wherein
as to two or more semiconductor chips, said diagnostic unit calculates a ratio of a consumed service life with respect to an expected service life or a ratio of a remaining service life with respect to an expected service life based on said deterioration amount, and
said output unit transmits a signal representing a ratio of said consumed service life of a semiconductor chip having a maximum ratio of said consumed service or a ratio of said remaining service life of a semiconductor chip having a minimum remaining service life from said output terminal to outside.

8. The power module according to claim 1, wherein
as to two or more semiconductor chips, said diagnostic unit calculates a ratio of a consumed service life with respect to an expected service life or a ratio of a remaining service life with respect to an expected service life based on said deterioration amount, and
said power module further comprises a select terminal to which a signal for selecting either a semiconductor chip having a shorter remaining service life or any of two or more semiconductor chips for which said ratio is calculated, and
when a semiconductor chip having a shortest remaining service life is selected, said output unit outputs a signal representing a ratio of said consumed service life of a semiconductor chip having a maximum ratio of said consumed service life, or a ratio of said remaining service life of a semiconductor having a minimum remaining service life, and when any of two or more semiconductor chips for which said ratio is calculated is selected, said output unit outputs a signal representing a ratio of said consumed service life of a selected semiconductor chip or a ratio of said remaining service life from said output terminal to outside.

9. The power module according to claim 1, wherein
as to two or more semiconductor chips, said diagnostic unit calculates a ratio of a consumed service life with respect to an expected service life or a ratio of a remaining service life with respect to an expected service life based on said deterioration amount, and
said power module further comprises a select terminal to which a signal for selecting either a semiconductor chip having a shortest remaining service life or all of two or more semiconductor chips for which said ratio is calculated, and
when a semiconductor chip having a shortest remaining service life is selected, said output unit outputs a signal representing a ratio of said consumed service life of a semiconductor chip having a maximum ratio of said consumed service life or a ratio of said remaining service life of a semiconductor chip having a minimum remaining service life from said output terminal to outside, and
when all of two or more semiconductor chips for which said ratio is calculated is selected, said output unit outputs a signal representing a ratio of said consumed service life of all of said semiconductor chips or a ratio of said remaining service life in time series from said output terminal to outside.

10. The power module according to claim 1, wherein
said power module further comprises six switching elements, and
one said temperature sensor is provided in a periphery of a semiconductor chip located at a center of three said switching elements of lower arms.

11. The power module according to claim 1, wherein
said power module further comprises six switching elements, and
said temperature sensor is provided in a periphery of each of three said switching elements of a lower arm.

12. The power module according to claim 1, wherein said power module further comprises an insulating element provided between said A/D converter and said diagnostic unit.

13. The power module according to claim 1, wherein
said power module further comprises:
six switching elements;
a current sensor which detects output currents for two phases among a U-phase, a V-phase, and a W-phase; and
a temperature estimating unit, and
said temperature sensor is provided in a periphery of a first switching element which is one of six switching elements, and
said temperature estimating unit
derives currents flowing to said six switching elements based on output currents for said two phases and based on if said six switching elements are in the on-state or off-state,
calculates a calorific value of each switching element based on a current flowing to each switching element,
calculates a reference temperature based on a calorific value of said first switching element and a temperature detected by said temperature sensor, and
sequentially selects switching elements other than said first switching element, and calculates a temperature of said selected switching element based said reference temperature and a calorific value of said selected switching element.

14. The power module according to claim 1, wherein said power module further comprises:
six switching elements which are semiconductor chips;
a current sensor which detects output currents of two phases among a U-phase, a V-phase, and a W-phase; and
a temperature estimating unit, wherein
said temperature sensor is provided in a periphery of three switching elements of lower arms among said six switching elements, and
said temperature estimating unit
derives currents flowing to said six switching elements based on output currents of said two phases and based on if said six switching elements are in the on-state or off-state,
calculates a calorific value of each switching element based on a current flowing to each switching element,
calculates a reference temperature based on calorific values of three switching elements of said lower arms and temperatures detected by said temperature sensor, and
sequentially selects switching elements other than three switching elements of said lower arms, and calculates temperatures of said selected switching elements based on said reference temperature and calorific values of said selected switching elements.

15. The power module according to claim 1, wherein said output unit generates a signal setting said diagnostic result to be an on-pulse or off-pulse duty ratio, and outputs said generated signal from said output terminal to outside.

16. The power module according to claim 1, wherein said output unit generates a serial signal including a digital value representing said diagnostic result, and outputs said generated signal from said output terminal to outside.

17. The power module according to claim 1, wherein said power module further comprises a select terminal which designates if said diagnostic result is outputted in an on-pulse or off-pulse duty ratio or outputted in a serial signal.

18. A power module, comprising:
a plurality of semiconductor chips;
one or more temperature sensor provided in a periphery of at least one semiconductor chip of the plurality of semiconductor chips;
one A/D converter which converts an output from the temperature sensor into a digital signal;
circuitry configured to
diagnose a service life of the power module based on a signal indicating a temperature outputted from the A/D converter, and
generate a signal representing a diagnostic result; and
an output terminal which outputs a signal representing the diagnostic result to outside, wherein
the circuitry is further configured to
calculate a deterioration degree of the semiconductor chip per power cycle from a service life characteristic in a power cycle of the semiconductor chip, and calculate a sum total of deterioration degrees of a plurality of power cycles as a deterioration amount, and
calculate a deterioration degree of the semiconductor Chip based on a maximum temperature, a minimum temperature, and a difference between the maximum temperature and the minimum temperature in one power cycle detected by the temperature sensor.

19. A diagnostic method of a power module, the power module including
a plurality of semiconductor chips,
one or more temperature sensor provided in a periphery of at least one semiconductor chip of said plurality of semiconductor chips,
one A/D converter which converts an output from said temperature sensor into a digital signal,
a diagnostic unit which diagnoses a service life of said power module based on a signal indicating a temperature outputted from said A/D converter,
an output unit which generates a signal representing a diagnostic result, and
an output terminal which outputs a signal representing said diagnostic result to outside,
the diagnostic method comprising:
calculating a deterioration degree of said semiconductor chip per power cycle from a service life characteristic in a power cycle of said semiconductor chip, and calculating a sum total of deterioration degrees of a plurality of power cycles as a deterioration amount by said diagnostic unit; and
calculating a deterioration degree of said semiconductor chip based on a maximum temperature, a minimum temperature, and a difference between said maximum temperature and said minimum temperature in one power cycle detected by said temperature sensor and diagnosing the deterioration degree of said semiconductor chip by said diagnostic unit.

* * * * *